United States Patent [19]
Lennox et al.

[11] Patent Number: 6,127,392
[45] Date of Patent: Oct. 3, 2000

[54] ANTHRANILIC ACID ANALOGS

[75] Inventors: Joseph Richard Lennox, Morrisville, N.C.; Schuyler Adam Antane, Lawrenceville; John Anthony Butera, Clarksburg, both of N.J.

[73] Assignee: American Home Products Corporation, Madison, N.J.

[21] Appl. No.: 09/127,753

[22] Filed: Aug. 3, 1998

Related U.S. Application Data

[60] Provisional application No. 60/054,901, Aug. 5, 1997.

[51] Int. Cl.$^7$ .......................... A01N 43/40; A01N 37/10; C07C 205/07; C07C 233/54; C07C 233/55
[52] U.S. Cl. .................. 514/352; 514/535; 514/563; 546/309; 546/310; 560/39; 560/45; 560/47; 562/426; 562/429; 562/430; 562/431; 562/432; 562/435; 562/456; 562/457; 562/458
[58] Field of Search ................................... 562/426, 429, 562/430, 431, 432, 456, 457, 458, 435; 514/352, 535, 563; 546/309, 310; 560/45, 47, 39

[56] References Cited

U.S. PATENT DOCUMENTS

| | | | |
|---|---|---|---|
| 5,438,046 | 8/1995 | Norcini et al. | 514/89 |
| 6,046,239 | 4/2000 | Lennox et al. | 514/563 |

FOREIGN PATENT DOCUMENTS

| | | |
|---|---|---|
| 0524781 | 1/1993 | European Pat. Off. |
| 0855387 | 8/1996 | European Pat. Off. |
| 200966 | 5/1988 | Hungary . |
| 49-42465 | 4/1974 | Japan . |
| 49-102692 | 9/1974 | Japan . |
| 57-179976 | 10/1982 | Japan . |
| 58-79436 | 5/1983 | Japan . |
| 60019754 | 7/1983 | Japan . |
| 5970654 | 4/1984 | Japan . |
| 60-097946 | 5/1985 | Japan . |
| 02218654 | 10/1988 | Japan . |
| 9422807 | 10/1994 | WIPO . |

OTHER PUBLICATIONS

Database CAPLUS on STN, Acc. No. 1997:265589, Harada et al., 'Preparation of acylaminobenzamide derivatives for the treatment of diseases caused by the supermultiplication of vascular intimal cells.' WO 9709301 (abstract), Mar. 13, 1997.

Rudy, B., Neuroscience, 25, 729–749 (1988).

Atwal, K., Medicinal Research Reviews, 12, 569–591 (1992).

Gopalakrishnan, M. et al., Drug Development Res., 28, 95–127 (1993).

Primeau J. et al., Current Pharma. Design, I, 391–406 (1995).

Edwards, G. et al., Exp. Opin. Invest. Drugs, 5(11), 1453–1464 (1996).

Strange, K. et al., Kidney International, 48, 994–1003 (1995).

Franciolini, F. et al., Biochimica et Biophysica Acta, 247 (1990).

Moerlein, S.M., Journal of Organometallic Chem., 319, 29–39 (1987).

*Primary Examiner*—Johann Richter
*Assistant Examiner*—Brian J. Davis
*Attorney, Agent, or Firm*—Rebbeca R. Barrett

[57] ABSTRACT

Compounds of the formula:

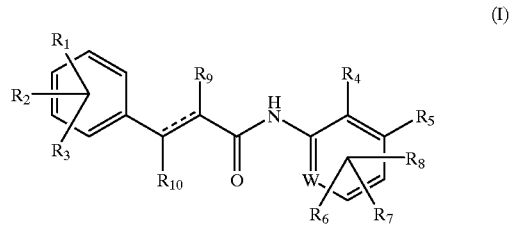

(I)

wherein:
$R_1$, $R_2$, $R_3$, $R_4$, $R_5$, $R_6$, $R_7$ and $R_8$ are, independently, hydrogen, $COOR_{15}$, halogen, nitro, cyano, $C_{1-10}$ alkoxy, $C_{1-10}$ haloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ haloalkyl, $C_{1-10}$ alkyl, $C_{2-12}$ alkenyl, $C_{6-12}$ aryl, $C_{6-12}$ aralkyl; with the proviso that at least one of $R_4$ and $R_5$ is $COOR_{15}$;

$R_9$ is hydrogen, $C_{1-10}$ alkyl and $C_{1-10}$ haloalkyl;

$R_{10}$ is hydrogen, $C_{1-10}$ alkyl, $C_{1-10}$ haloalkyl, or $C_{2-12}$ alkylidene;

$R_{15}$ is hydrogen, metal cation, acetylamido, alkoxyacetoyl or a related moiety which delivers the carboxylate in vivo;

the dotted line is an optional double bond; with the proviso that when $R_{10}$ is an alkylidene moiety, the double bond is absent; and W is nitrogen or carbon bearing a hydrogen, or $R_4$, $R_5$ or $R_6$ as hereinbefore defined; or pharmaceutcal salts thereof, are useful in the treatment of disorders associated with smooth muscle contraction via potassium channel and chloride channel modulation.

29 Claims, 3 Drawing Sheets

ANTHRANILIC ACID ANALOGS

This application claims the benefit of U.S. Provisional Application No. 60/054,901, filed Aug. 5, 1997.

BACKGROUND OF INVENTION

The present invention relates to a novel series of anthranilic acid-derived amides (I) having pharmacological activity, to a process for their preparation, to pharmaceutical compositions containing them, and to their use in the treatment of disorders associated with smooth muscle contraction, via potassium channel and chloride channel modulation. Such disorders include, but are not limited to: urinary incontinence, asthma, premature labor, irritable bowel syndrome, congestive heart failure, angina, and cerebral vascular disease.

Modulation of potassium channels remains at the forefront of current approaches for controlling resting cell membrane potential and affecting cell excitability. A wide variety of discrete potassium channels exist and these have been thoroughly classified according to structure, function, pharmacological properties, and gating mechanisms in several recent reviews [Rudy, B. *Neuroscience* 1988, 25, 729–749; Atwal, K., *Medicinal Research Reviews* 1992, 12, 569–591; Gopalakrishnan, M. et al., *Drug Development Research* 1993, 28, 95–127; Primeau, J. et al. *Current Pharmaceutical Design* 1995, 1, 391–406; Edwards, G. et al. *Exp. Opin. Invest. Drugs* 1996, 5 (11), 1453–1464]. Therapeutic potential for potassium channel modulators in cardiovascular disorders, metabolic disorders, central nervous system disorders, bronchial asthma, and irritable bladder is being vastly explored.

Research interests in the modulation of chloride channels are growing at a fast pace [Strange, K. et al. *Kidney International* 1995, 48, 994–1003; Franciolini, F. et al. *Biochimica et Biophysica Acta* 1990, 247]. Various disease states potentially amenable to chloride channel modulation include bronchial asthma, cardiac arrhythmias, cystic fibrosis, and kidney disease.

Harita et al. disclose a process for the manufacturing of a class of meta-substituted aromatic amide carboxylic acid derivatives in Japanese Patent Application No. 49-102692, and also builds on a method for manufacturing aromatic cinnammic acid derivatives in Japanese Patent Application No. 49-42465. Several patents and patent applications focus particularly on agents possessing claims of anti-allergic/anti-asthmatic/anti-histaminic activity: Sato et al. report a group of anthranilic acid derivatives (highlighting Tranilast® as an anti-allergic-agent) in Japanese Patent Application No. 57-179976; related to these anthranilates is a claim by Aoyanagi et. al. in Japanese Patent Application No. 58-79436 which discloses a method for manufacturing anthranilic acid derivatives; also related is Hungarian Patent HU 200 996 B which emphasizes the production of several Tranilast® analogs; and Yukihiko, in Japanese Patent No. J6 0019-754-A, has also indicated a method for the preparation of anthranilic acid derivatives where the styrenyl portion is strictly limited to alkoxy, hydroxy or acyloxy.

In addition, Japanese Patent No. J0 2218-654-A by Tsumoro et al. which reveals a class of amino-benzoic acid derivatives which are useful as reverse transcriptase inhibitors. Also by Tsumoro et al., Patent No. J6 0097-946-A discloses a series of substituted carboxamide derivatives which exhibit activity as leucotriene antagonists and phospholipase inhibitors.

BRIEF DESCRIPTION OF THE FIGURES

FIG. 1 is a schematic representation of a single cell recordings of cell current.

FIG. 2 is a schematic representation of the effects of Example 1 on chloride channel current induced by swelling.

DESCRIPTION OF THE INVENTION

Figure 1A:
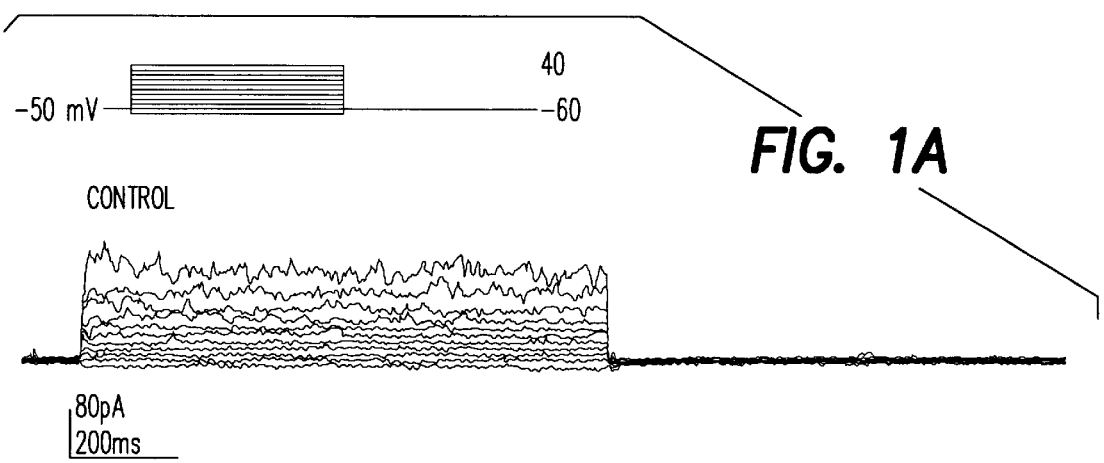
FIG. 1A shows cell outward current of the control.

In accordance with the present invention, there is provided compounds represented by the formula:

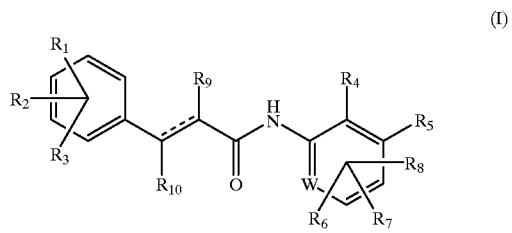

(I)

wherein:
$R_1$, $R_2$, $R_3$, $R_4$,$R_5$, $R_6$, $R_7$ and $R_8$ are, independently, hydrogen, $COOR_{15}$, halogen, nitro, cyano, $C_{1-10}$ alkoxy, $C_{1-10}$ haloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ haloalkyl, $C_{1-10}$ alkyl, $C_{2-12}$ alkenyl, $C_{6-12}$ aryl, $C_{6-12}$ aralkyl; with the proviso that at least one of $R_4$ and $R_5$ is $COOR_{15}$;

$R_9$ is hydrogen, $C_{1-10}$ alkyl and $C_{1-10}$ haloalkyl;

$R_{10}$ is hydrogen, $C_{1-10}$ alkyl, $C_{1-10}$ haloalkyl, or $C_{2-12}$ alkylidene;

$R_{15}$ is hydrogen, metal cation, acetylamido, alkoxyacetoyl or a related moiety which delivers the carboxylate in vivo;

the dotted line is an optional double bond; with the proviso that when $R_{10}$ is an alkylidene moiety, the bond is absent; and W is nitrogen or carbon bearing a hydrogen, or $R_4$, $R_5$ or $R_6$ as hereinbefore defined; or pharmaceutcal salts thereof.

In some preferred embodiments $R_1$, $R_2$ and $R_3$ are, independently, hydrogen, cyano, $C_{1-10}$ perhaloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ perhaloalkyl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$, $R_6$, $R_7$ and $R_8$ are, independently, hydrogen, $COOR_{15}$, halogen, nitro, cyano, $C_{1-10}$ alkoxy, $C_{1-10}$ haloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ haloalkyl, $C_{1-10}$ alkyl, $C_{2-10}$ alkenyl, $C_{6-12}$ aryl, and $C_{6-12}$ aralkyl, with the proviso that at least one of $R_4$ and $R_5$ is $COOR_{15}$;

$R_9$ is hydrogen, $C_{1-10}$ alkyl and $C_{1-10}$ haloalkyl;

$R_{10}$ is hydrogen, $C_{1-10}$ alkyl, $C_{1-10}$ haloalkyl, or $C_{2-12}$ alkylidene;

$R_{15}$ is hydrogen, metal cation, acetylamido, alkoxyacetoyl or a related moiety which delivers the carboxylate in vivo; the dotted line is an optional double bond; with the proviso that when $R_{10}$ is an alkylidene moiety, the bond is absent; and W is nitrogen or carbon bearing a hydrogen, or $R_4$, $R_5$ or $R_6$ as hereinbefore defined; or pharmaceutical salts thereof.

In other preferred aspects of this invention $R_{15}$ is selected from the group consisting of hydrogen, a metal cation, a moiety selected from:

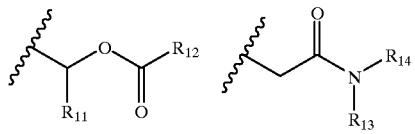

wherein $R_{11}$, $R_{12}$, $R_{13}$, and $R_{14}$ are, independently, hydrogen, $C_{1-10}$ alkyl, $C_{6-12}$ aryl, or $C_{6-12}$ aralkyl.

In still other preferred embodiments of the present invention, W is nitrogen, or a carbon bearing one of hydrogen, halogen, nitro, cyano, or $C_{1-10}$ haloalkyl. More preferably W is carbon bearing a hydrogen.

In some aspects of the invention it is preferred that $R_1$, $R_2$, $R_3$, $R_4$, $R_5$, $R_6$, $R_7$ and $R_8$ are, independently, selected from hydrogen, halogen, $COOR_{15}$, nitro, cyano, $C_{1-6}$ alkoxy, $C_{1-6}$ alkanoyl, $C_{1-6}$ haloalkoxy, $C_{6-10}$ aryloyl, $C_{1-6}$ alkylsulfonyl, $C_{1-6}$ haloalkylsulfonyl, $C_{6-10}$ arylsulfonyl, $C_{1-6}$ haloalkyl, $C_{1-6}$ alkyl, amino, and $C_{1-6}$ dialkylamino, with the provisos that (1) $R_1$, $R_2$ and $R_3$ may not simultaneously be hydrogen, (2) when $R_1$ and $R_2$ are hydrogen, $R_3$ is not meta-$CF_3$, and (3) at least one of $R_4$ and $R_5$ is $COOR_{15}$.

It is also preferred in some aspects of the invention that $R_1$, $R_2$ and $R_3$ are selected from hydrogen, $C_{1-6}$ alkyl, $C_{1-6}$ haloalkyl, $C_{1-6}$ alkoxy, nitro, $C_{1-6}$ dialkylamino and halogen with the provisos that (1) $R_1$, $R_2$ and $R_3$ may not simultaneously be hydrogen and (2) when $R_1$ and $R_2$ are hydrogen, $R_3$ is not meta-CF3. With the foregoing provisos, it is further preferred that at least one of $R_1$, $R_2$ and $R_3$ is perhaloalkyl more preferably trifluoromethyl. Where one of $R_1$, $R_2$ and $R_3$ is perhaloalkyl, it is preferred that said substituent is 4-$CF_3$.

In still other preferred embodiments of the present invention, it is preferred that one of $R_6$, $R_7$ and $R_8$ is a halogen, more preferably chloro and most preferably 4-chloro.

In yet other embodiments of the present invention, it is preferred that $R_4$ is $COOR_{15}$, and more preferably COOH.

In some preferrred embodiments of the present invention, $R_{10}$ is alkylidene and more preferably methylidene. In still other embodiments of the present invention $R_9$ is $C_{1-6}$ alkyl and most preferably methyl. The double bond is present in preferred embodiments of the invention.

Preferred compounds of the present invention are:

(E)-2-[2-Methyl-3-(4-trifluoromethyl-phenyl)-acryloylamino]-benzoic acid lithium salt;
2-[3-(4-Trifluoromethyl-phenyl)propionyl-amino]-benzoic acid;
(E)-2-[3-(4-Bromo-phenyl)-acryloylamino]-benzoic acid;
(E)-2-[3[(4-Trifluoromethyl-phenyl)acryloyl-amino]-benzoic acid;
(E)-2-[3[(4-Trifluoromethyl-phenyl)-acryloylamino]-benzoic acid lithium salt hemihydrate;
2-[3-(4-Trifluoromethyl-phenyl)-but-3-enoylamino]-benzoic acid;
(E)-2-[3-(4-Trifluoromethyl-phenyl)-but-2-enoylamino]-benzoic acid sodium salt;
(E)-5-Chloro-2-[2-methyl-3-(4-trifluoromethyl-phenyl)-acryloylamino-benzoic acid;
(E)-5-Chloro-2-[2-methyl-3-(4-trifluoromethyl-phenyl)-acryloylamino]-benzoic acid lithium salt hemihydrate;
(E)-4-Chloro-2-[2-methyl-3-(4-trifluoromethyl-phenyl)-acryloylamino]-benzoic acid;
(E)-4-Chloro-2-[2-methyl-3-(4-trifluoromethyl-phenyl)-acryloylamino]-benzoic acid lithium salt hemihydrate;
(E)-2-[2-Methyl-3-(4-trifluoromethyl-phenyl)-acryloylamino]-nicotinic acid;
(E)-5-Methoxy-2-[2-methyl-3-(4-trifluoromethyl-phenyl)-acryloylamino]-benzoic acid;
(E)-2-[2-Methyl-3-(4-trifluoromethyl-phenyl)-acryloylamino]-benzoic acid diethyl-carbamoylmethyl ester;
2-(3-o-Tolyl-acryloylamino)-benzoic acid;
2-(2-Methyl-3-o-tolyl-acryloylamino)-benzoic acid;
3-(3-o-Tolyl-acryloylamino)-benzoic acid;
3-(2-Methyl-3-o-tolyl-acryloylamino)-benzoic acid;
4-Chloro-2-(3-o-tolyl-acryloylamino)-benzoic acid;
4-Chloro-2-(2-methyl-3-o-tolyl-acryloylamino)-benzoic acid;
4-Chloro-3-(3-o-tolyl-acryloylamino)-benzoic acid;
4-Chloro-3-(2-methyl-3-o-tolyl-acryloylamino)-benzoic acid;
5-Chloro-2-(3-o-tolyl-acryloylamino)-benzoic acid;
5-Chloro-2-(2-methyl-3-o-tolyl-acryloylamino)-benzoic acid;
2-(3-m-Tolyl-acryloylamino)-benzoic acid;
2-(2-Methyl-3-m-tolyl-acryloylamino)-benzoic acid;
3-(3-m-Tolyl-acryloylamino)-benzoic acid;
3-(2-Methyl-3-m-tolyl-acryloylamino)-benzoic acid;
4-Chloro-2-(3-m-tolyl-acryloylamino)-benzoic acid;
4-Chloro-3-(3-m-tolyl-acryloylamino)-benzoic acid;
4-Chloro-3-(2-methyl-3-m-tolyl-acryloylamino)-benzoic acid;
5-Chloro-2-(3-m-tolyl-acryloylamino)-benzoic acid;
5-Chloro-2-(2-methyl-3-m-tolyl-acryloylamino)-benzoic acid;
2-(3-p-Tolyl-acryloylamino)-benzoic acid;
2-(2-Methyl-3-p-tolyl-acryloylamino)-benzoic acid;
3-(3-p-Tolyl-acryloylamino)-benzoic acid;
3-(2-Methyl-3-p-tolyl-acryloylamino)-benzoic acid;
4-Chloro-2-(3-p-tolyl-acryloylamino)-benzoic acid;
4-Chloro-2-(2-methyl-3-p-tolyl-acryloylamino)-benzoic acid;
4-Chloro-3-(3-p-tolyl-acryloylamino)-benzoic acid;
4-Chloro-3-(2-methyl-3-p-tolyl-acryloylamino)-benzoic acid;
5-Chloro-2-(3-p-tolyl-acryloylamino)-benzoic acid;
5-Chloro-2-(2-methyl-3-p-tolyl-acryloylamino)-benzoic acid;
2-[3-(2-Fluoro-phenyl)-acryloylamino]-benzoic acid;
2-[3-(2-Fluoro-phenyl)-2-methyl-acryloylamino]-benzoic acid;

3-[3-(2-Fluoro-phenyl)-acryloylamino]-benzoic acid;
3-[3-(2-Fluoro-phenyl)-2-methyl-acryloylamino]-benzoic acid;
4-Chloro-2-[3-(2-fluoro-phenyl)-acryloylamino]-benzoic acid;
4-Chloro-2-[3-(2-fluoro-phenyl)-2-methyl-acryloylamino]-benzoic acid;
4-Chloro-3-[3-(2-fluoro-phenyl)-acryloylamino]-benzoic acid;
4-Chloro-3-[3-(2-fluoro-phenyl)-2-methyl-acryloylamino]-benzoic acid;
5-Chloro-2-[3-(2-fluoro-phenyl)-acryloylamino]-benzoic acid;
5-Chloro-2-[3-(2-fluoro-phenyl)-2-methyl-acryloylamino]-benzoic acid;
2-[3-(3-Fluoro-phenyl)-acryloylamino]-benzoic acid;
2-[3-(3-Fluoro-phenyl)-2-methyl-acryloylamino]-benzoic acid;
3-[3-(3-Fluoro-phenyl)-acryloylamino]-benzoic acid;
3-[3-(3-Fluoro-phenyl)-2-methyl-acryloylamino]-benzoic acid;
4-Chloro-2-[3-(3-fluoro-phenyl)-acryloylamino]-benzoic acid;
4-Chloro-2-[3-(3-fluoro-phenyl)-2-methyl-acryloylamino]-benzoic acid;
4-Chloro-3-[3-(3-fluoro-phenyl)-acryloylamino]-benzoic acid;
4-Chloro-3-[3-(3-fluoro-phenyl)-2-methyl-acryloylamino]-benzoic acid;
5-Chloro-2-[3-(3-fluoro-phenyl)-acryloylamino]-benzoic acid;
5-Chloro-2-[3-(3-fluoro-phenyl)-2-methyl-acryloylamino]-benzoic acid;
2-[3-(4-Fluoro-phenyl)-acryloylamino]-benzoic acid;
2-[3-(4-Fluoro-phenyl)-2-methyl-acryloylamino]-benzoic acid;
3-[3-(4-Fluoro-phenyl)-acryloylamino]-benzoic acid;
3-[3-(4-Fluoro-phenyl)-2-methyl-acryloylamino]-benzoic acid;
4-Chloro-2-[3-(4-fluoro-phenyl)-acryloylamino]-benzoic acid;
4-Chloro-2-[3-(4-fluoro-phenyl)-2-methyl-acryloylamino]-benzoic acid;
4-Chloro-3-[3-(4-fluoro-phenyl)-acryloylamino]-benzoic acid;
4-Chloro-3-[3-(4-fluoro-phenyl)-2-methyl-acryloylamino]-benzoic acid;
5-Chloro-2-[3-(4-fluoro-phenyl)-acryloylamino]-benzoic acid;
5-Chloro-2-[3-(4-fluoro-phenyl)-2-methyl-acryloylamino]-benzoic acid;
2-[3-(2-Chloro-phenyl)-acryloylamino]-benzoic acid;
2-[3-(2-Chloro-phenyl)-2-methyl-acryloylamino]-benzoic acid;
3-[3-(2-Chloro-phenyl)-acryloylamino]-benzoic acid;
3-[3-(2-Chloro-phenyl)-2-methyl-acryloylamino]-benzoic acid;
4-Chloro-2-[3-(2-chloro-phenyl)-acryloylamino]-benzoic acid;
4-Chloro-2-[3-(2-chloro-phenyl)-2-methyl-acryloylamino]-benzoic acid;
4-Chloro-3-[3-(2-chloro-phenyl)-acryloylamino]-benzoic acid;
4-Chloro-3-[3-(2-chloro-phenyl)-2-methyl-acryloylamino]-benzoic acid;
5-Chloro-2-[3-(2-chloro-phenyl)-acryloylamino]-benzoic acid;
5-Chloro-2-[3-(2-chloro-phenyl)-2-methyl-acryloylamino]-benzoic acid;
2-[3-(3-Chloro-phenyl)-acryloylamino]-benzoic acid;
2-[3-(3-Chloro-phenyl)-2-methyl-acryloylamino]-benzoic acid;
3-[3-(3-Chloro-phenyl)-acryloylamino]-benzoic acid;
3-[3-(3-Chloro-phenyl)-2-methyl-acryloylamino]-benzoic acid;
4-Chloro-2-[3-(3-chloro-phenyl)-acryloylamino]-benzoic acid;
4-Chloro-2-[3-(3-chloro-phenyl)-2-methyl-acryloylamino]-benzoic acid;
4-Chloro-3-[3-(3-chloro-phenyl)-acryloylamino]-benzoic acid;
4-Chloro-3-[3-(3-chloro-phenyl)-2-methyl-acryloylamino]-benzoic acid;
5-Chloro-2-[3-(3-chloro-phenyl)-acryloylamino]-benzoic acid;
5-Chloro-2-[3-(3-chloro-phenyl)-2-methyl-acryloylamino]-benzoic acid;
2-[3-(2-Bromo-phenyl)-acryloylamino]-benzoic acid;
2-[3-(2-Bromo-phenyl)-2-methyl-acryloylamino]-benzoic acid;
2-[3-(2-Bromo-phenyl)-2-methyl-acryloylamino]-benzoic acid;
3-[3-(2-Bromo-phenyl)-acryloylamino]-benzoic acid;
3-[3-(2-Bromo-phenyl)-2-methyl-acryloylamino]-benzoic acid;
2-[3-(2-Bromo-phenyl)-acryloylamino]-4-chloro-benzoic acid;
2-[3-(2-Bromo-phenyl)-2-methyl-acryloylamino]-4-chloro-benzoic acid;
3-[3-(2-Bromo-phenyl)-acryloylamino]-4-chloro-benzoic acid;
3-[3-(2-Bromo-phenyl)-2-methyl-acryloylamino]-4-chloro-benzoic acid;
2-[3-(2-Bromo-phenyl)-acryloylamino]-5-chloro-benzoic acid;
2-[3-(2-Bromo-phenyl)-2-methyl-acryloylamino]-5-chloro-benzoic acid;
2-[3-(3-Bromo-phenyl)-acryloylamino]-benzoic acid;
2-[3-(3-Bromo-phenyl)-2-methyl-acryloylamino]-benzoic acid;;3-[3-(3-Bromo-phenyl)-acryloylamino]-benzoic acid;
3-[3-(3-Bromo-phenyl)-2-methyl-acryloylamino]-benzoic acid;
2-[3-(3-Bromo-phenyl)-acryloylamino]-4-chloro-benzoic acid;
2-[3-(3-Bromo-phenyl)-2-methyl-acryloylamino]-4-chloro-benzoic acid;
3-[3-(3-Bromo-phenyl)-acryloylamino]-4-chloro-benzoic acid;
3-[3-(3-Bromo-phenyl)-2-methyl-acryloylamino]-4-chloro-benzoic acid;
2-[3-(3-Bromo-phenyl)-acryloylamino]-5-chloro-benzoic acid;
2-[3-(3-Bromo-phenyl)-2-methyl-acryloylamino]-5-chloro-benzoic acid;
2-[3-(2-Trifluoromethyl-phenyl)-acryloylamino]-benzoic acid;
2-[2-Methyl-3-(2-trifluoromethyl-phenyl)-acryloylamino]-benzoic acid;
3-[3-(2-Trifluoromethyl-phenyl)-acryloylamino]-benzoic acid;
3-[2-Methyl-3-(2-trifluoromethyl-phenyl)-acryloylamino]-benzoic acid;
4-Chloro-2-[3-(2-trifluoromethyl-phenyl)-acryloylamino]-benzoic acid;

4-Chloro-2-[2-methyl-3-(2-trifluoromethyl-phenyl)-acryloylamino]-benzoic acid;
4-Chloro-3-[3-(2-trifluoromethyl-phenyl)-acryloylamino]-benzoic acid;
4-Chloro-3-[2-methyl-3-(2-trifluoromethyl-phenyl)-acryloylamino]-benzoic acid;
5-Chloro-2-[3-(2-trifluoromethyl-phenyl)-acryloylamino]-benzoic acid;
5-Chloro-2-[2-methyl-3-(2-trifluoromethyl-phenyl)-acryloylamino]-benzoic acid;
2-[3-(3-Trifluoromethyl-phenyl)-acryloylamino]-benzoic acid;
2-[2-Methyl-3-(3-trifluoromethyl-phenyl)-acryloylamino]-benzoic acid;
3-[3-(3-Trifluoromethyl-phenyl)-acryloylamino]-benzoic acid;
3-[2-Methyl-3-(3-trifluoromethyl-phenyl)-acryloylamino]-benzoic acid;
4-Chloro-2-[3-(3-trifluoromethyl-phenyl)-acryloylamino]-benzoic acid;
4-Chloro-2-[2-methyl-3-(3-trifluoromethyl-phenyl)-acryloylamino]-benzoic acid;
4-Chloro-3-[3-(3-trifluoromethyl-phenyl)-acryloylamino]-benzoic acid;
4-Chloro-3-[2-methyl-3-(3-trifluoromethyl-phenyl)-acryloylamino]-benzoic acid;
5-Chloro-2-[3-(3-trifluoromethyl-phenyl)-acryloylamino]-benzoic acid;
5-Chloro-2-[2-methyl-3-(3-trifluoromethyl-phenyl)-acryloylamino]-benzoic acid;
2-[3-(4-Trifluoromethyl-phenyl)-acryloylamino]-benzoic acid;
2-[2-Methyl-3-(4-trifluoromethyl-phenyl)-acryloylamino]-benzoic acid;
3-[3-(4-Trifluoromethyl-phenyl)-acryloylamino]-benzoic acid;
3-[2-Methyl-3-(4-trifluoromethyl-phenyl)-acryloylamino]-benzoic acid;
4-Chloro-2-[3-(4-trifluoromethyl-phenyl)-acryloylamino]-benzoic acid;
4-Chloro-2-[2-methyl-3-(4-trifluoromethyl-phenyl)-acryloylamino]-benzoic acid;
4-Chloro-3-[3-(4-trifluoromethyl-phenyl)-acryloylamino]-benzoic acid;
4-Chloro-3-[2-methyl-3-(4-trifluoromethyl-phenyl)-acryloylamino]-benzoic acid;
5-Chloro-2-[3-(4-trifluoromethyl-phenyl)-acryloylamino]-benzoic acid;
5-Chloro-2-[2-methyl-3-(4-trifluoromethyl-phenyl)-acryloylamino]-benzoic acid;
2-(3-Phenyl-acryloylamino)-benzoic acid;
2-(2-Methyl-3-phenyl-acryloylamino)-benzoic acid;
3-(3-Phenyl-acryloylamino)-benzoic acid;
3-(2-Methyl-3-phenyl-acryloylamino)-benzoic acid;
4-Chloro-2-(3-phenyl-acryloylamino)-benzoic acid;
4-Chloro-2-(2-methyl-3-phenyl-acryloylamino)-benzoic acid;
4-Chloro-3-(3-phenyl-acryloylamino)-benzoic acid;
4-Chloro-3-(2-methyl-3-phenyl-acryloylamino)-benzoic acid;
5-Chloro-2-(3-phenyl-acryloylamino)-benzoic acid;
5-Chloro-2-(2-methyl-3-phenyl-acryloylamino)-benzoic acid;
2-[3-(4-Chloro-phenyl)-acryloylamino]-benzoic acid;
2-[3-(4-Chloro-phenyl)-2-methyl-acryloylamino]-benzoic acid;
3-[3-(4-Chloro-phenyl)-acryloylamino]-benzoic acid;
3-[3-(4-Chloro-phenyl)-2-methyl-acryloylamino]-benzoic acid;
4-Chloro-2-[3-(4-chloro-phenyl)-acryloylamino]-benzoic acid;
4-Chloro-2-[3-(4-chloro-phenyl)-2-methyl-acryloylamino]-benzoic acid;
4-Chloro-3-[3-(4-chloro-phenyl)-acryloylamino]-benzoic acid;
4-Chloro-3-[3-(4-chloro-phenyl)-2-methyl-acryloylamino]-benzoic acid;
5-Chloro-2-[3-(4-chloro-phenyl)-acryloylamino]-benzoic acid;
5-Chloro-2-[3-(4-chloro-phenyl)-2-methyl-acryloylamino]-benzoic acid;
2-[3-(4-Bromo-phenyl)-acryloylamino]-benzoic acid;
2-[3-(4-Bromo-phenyl)-2-methyl-acryloylamino]-benzoic acid;
3-[3-(4-Bromo-phenyl)-acryloylamino]-benzoic acid;
3-[3-(4-Bromo-phenyl)-2-methyl-acryloylamino]-benzoic acid;
2-[3-(4-Bromo-phenyl)-acryloylamino]-4-chloro-benzoic acid;
2-[3-(4-Bromo-phenyl)-2-methyl-acryloylamino]-4-chloro-benzoic acid;
3-[3-(4-Bromo-phenyl)-acryloylamino]-4-chloro-benzoic acid;
3-[3-(4-Bromo-phenyl)-2-methyl-acryloylamino]-4-chloro-benzoic acid;
2-[3-(4-Bromo-phenyl)-acryloylamino]-5-chloro-benzoic acid;
2-[3-(4-Bromo-phenyl)-2-methyl-acryloylamino]-5-chloro-benzoic acid;
2-[3-(2-Methoxy-phenyl)-acryloylamino]-benzoic acid;
2-[3-(2-Methoxy-phenyl)-2-methyl-acryloylamino]-benzoic acid;
3-[3-(2-Methoxy-phenyl)-acryloylamino]-benzoic acid;
3-[3-(2-Methoxy-phenyl)-2-methyl-acryloylamino]-benzoic acid;
4-Chloro-2-[3-(2-methoxy-phenyl)-acryloylamino]-benzoic acid;
4-Chloro-2-[3-(2-methoxy-phenyl)-2-methyl-acryloylamino]-benzoic acid;
4-Chloro-3-[3-(2-methoxy-phenyl)-acryloylamino]-benzoic acid;
4-Chloro-3-[3-(2-methoxy-phenyl)-2-methyl-acryloylamino]-benzoic acid;
5-Chloro-2-[3-(2-methoxy-phenyl)-acryloylamino]-benzoic acid;
5-Chloro-2-[3-(2-methoxy-phenyl)-2-methyl-acryloylamino]-benzoic acid;
2-[3-(3-Methoxy-phenyl)-acryloylamino]-benzoic acid;
2-[3-(3-Methoxy-phenyl)-2-methyl-acryloylamino]-benzoic acid;
3-[3-(3-Methoxy-phenyl)-acryloylamino]-benzoic acid;
3-[3-(3-Methoxy-phenyl)-2-methyl-acryloylamino]-benzoic acid;
4-Chloro-2-[3-(3-methoxy-phenyl)-acryloylamino]-benzoic acid;
4-Chloro-2-[3-(3-methoxy-phenyl)-2-methyl-acryloylamino]-benzoic acid;
4-Chloro-3-[3-(3-methoxy-phenyl)-acryloylamino]-benzoic acid;
4-Chloro-3-[3-(3-methoxy-phenyl)-2-methyl-acryloylamino]-benzoic acid;
5-Chloro-2-[3-(3-methoxy-phenyl)-acryloylamino]-benzoic acid;
5-Chloro-2-[3-(3-methoxy-phenyl)-2-methyl-acryloylamino]-benzoic acid;

2-[3-(4-Methoxy-phenyl)-acryloylamino]-benzoic acid;
2-[3-(4-Methoxy-phenyl)-2-methyl-acryloylamino]-benzoic acid;
3-[3-(4-Methoxy-phenyl)-acryloylamino]-benzoic acid;
3-[3-(4-Methoxy-phenyl)-2-methyl-acryloylamino]-benzoic acid;
4-Chloro-2-[3-(4-methoxy-phenyl)-acryloylamino]-benzoic acid;
4-Chloro-2-[3-(4-methoxy-phenyl)-2-methyl-acryloylamino]-benzoic acid;
4-Chloro-3-[3-(4-methoxy-phenyl)-acryloylamino]-benzoic acid;
4-Chloro-3-[3-(4-methoxy-phenyl)-2-methyl-acryloylamino]-benzoic acid;
5-Chloro-2-[3-(4-methoxy-phenyl)-acryloylamino]-benzoic acid;
5-Chloro-2-[3-(4-methoxy-phenyl)-2-methyl-acryloylamino]-benzoic acid;
2-[3-(2-Nitro-phenyl)-acryloylamino]-benzoic acid;
2-[2-Methyl-3-(2-nitro-phenyl)-acryloylamino]-benzoic acid;
3-[3-(2-Nitro-phenyl)-acryloylamino]-benzoic acid;
3-[2-Methyl-3-(2-nitro-phenyl)-acryloylamino]-benzoic acid;
4-Chloro-2-[3-(2-nitro-phenyl)-acryloylamino]-benzoic acid;
4-Chloro-2-[2-methyl-3-(2-nitro-phenyl)-acryloylamino]-benzoic acid;
4-Chloro-3-[3-(2-nitro-phenyl)-acryloylamino]-benzoic acid;
4-Chloro-3-[2-methyl-3-(2-nitro-phenyl)-acryloylamino]-benzoic acid;
5-Chloro-2-[3-(2-nitro-phenyl)-acryloylamino]-benzoic acid;
5-Chloro-2-[2-methyl-3-(2-nitro-phenyl)-acryloylamino]-benzoic acid;
2-[3-(3-Nitro-phenyl)-acryloylamino]-benzoic acid;
2-[2-Methyl-3-(3-nitro-phenyl)-acryloylamino]-benzoic acid;
3-[3-(3-Nitro-phenyl)-acryloylamino]-benzoic acid;
3-[2-Methyl-3-(3-nitro-phenyl)-acryloylamino]-benzoic acid;
4-Chloro-2-[3-(3-nitro-phenyl)-acryloylamino]-benzoic acid;
4-Chloro-2-[2-methyl-3-(3-nitro-phenyl)-acryloylamino]-benzoic acid;
4-Chloro-3-[3-(3-nitro-phenyl)-acryloylamino]-benzoic acid;
4-Chloro-3-[2-methyl-3-(3-nitro-phenyl)-acryloylamino]-benzoic acid;
5-Chloro-2-[3-(3-nitro-phenyl)-acryloylamino]-benzoic acid;
5-Chloro-2-[2-methyl-3-(3-nitro-phenyl)-acryloylamino]-benzoic acid;
2-[3-(4-Nitro-phenyl)-acryloylamino]-benzoic acid;
2-[2-Methyl-3-(4-nitro-phenyl)-acryloylamino]-benzoic acid;
3-[3-(4-Nitro-phenyl)-acryloylamino]-benzoic acid;
3-[2-Methyl-3-(4-nitro-phenyl)-acryloylamino]-benzoic acid;
4-Chloro-2-[3-(4-nitro-phenyl)-acryloylamino]-benzoic acid;
4-Chloro-2-[2-methyl-3-(4-nitro-phenyl)-acryloylamino]-benzoic acid;
4-Chloro-3-[3-(4-nitro-phenyl)-acryloylamino]-benzoic acid;
4-Chloro-3-[2-methyl-3-(4-nitro-phenyl)-acryloylamino]-benzoic acid;
5-Chloro-2-[3-(4-nitro-phenyl)-acryloylamino]-benzoic acid;
5-Chloro-2-[2-methyl-3-(4-nitro-phenyl)-acryloylamino]-benzoic acid;
2-[3-(4-Dimethylamino-phenyl)-acryloylamino]-benzoic acid;
2-[3-(4-Dimethylamino-phenyl)-2-methyl-acryloylamino]-benzoic acid;
3-[3-(4-Dimethylamino-phenyl)-acryloylamino]-benzoic acid;
3-[3-(4-Dimethylamino-phenyl)-2-methyl-acryloylamino]-benzoic acid;
4-Chloro-2-[3-(4-dimethylamino-phenyl)-acryloylamino]-benzoic acid;
4-Chloro-2-[3-(4-dimethylamino-phenyl)-2-methyl-acryloylamino]-benzoic acid;
4-Chloro-3-[3-(4-dimethylamino-phenyl)-acryloylamino]-benzoic acid;
4-Chloro-3-[3-(4-dimethylamino-phenyl)-2-methyl-acryloylamino]-benzoic acid;
5-Chloro-2-[3-(4-dimethylamino-phenyl)-acryloylamino]-benzoic acid;
5-Chloro-2-[3-(4-dimethylamino-phenyl)-2-methyl-acryloylamino]-benzoic acid;
2-[3-(2,4-Dichloro-phenyl)-acryloylamino]-benzoic acid;
2-[3-(2,4-Dichloro-phenyl)-2-methyl-acryloylamino]-benzoic acid;
3-[3-(2,4-Dichloro-phenyl)-acryloylamino]-benzoic acid;
3-[3-(2,4-Dichloro-phenyl)-2-methyl-acryloylamino]-benzoic acid;
4-Chloro-2-[3-(2,4-dichloro-phenyl)-acryloylamino]-benzoic acid;
4-Chloro-2-[3-(2,4-dichloro-phenyl)-2-methyl-acryloylamino]-benzoic acid;
4-Chloro-3-[3-(2,4-dichloro-phenyl)-acryloylamino]-benzoic acid;
4-Chloro-3-[3-(2,4-dichloro-phenyl)-2-methyl-acryloylamino]-benzoic acid;
5-Chloro-2-[3-(2,4-dichloro-phenyl)-acryloylamino]-benzoic acid;
5-Chloro-2-[3-(2,4-dichloro-phenyl)-2-methyl-acryloylamino]-benzoic acid;
2-[3-(3,4-Dichloro-phenyl)-acryloylamino]-benzoic acid;
2-[3-(3,4-Dichloro-phenyl)-2-methyl-acryloylamino]-benzoic acid;
3-[3-(3,4-Dichloro-phenyl)-acryloylamino]-benzoic acid;
3-[3-(3,4-Dichloro-phenyl)-2-methyl-acryloylamino]-benzoic acid;
4-Chloro-2-[3-(3,4-dichloro-phenyl)-acryloylamino]-benzoic acid;
4-Chloro-2-[3-(3,4-dichloro-phenyl)-2-methyl-acryloylamino]-benzoic acid;
4-Chloro-3-[3-(3,4-dichloro-phenyl)-acryloylamino]-benzoic acid;
4-Chloro-3-[3-(3,4-dichloro-phenyl)-2-methyl-acryloylamino]-benzoic acid;
5-Chloro-2-[3-(3,4-dichloro-phenyl)-acryloylamino]-benzoic acid; and
5-Chloro-2-[3-(3,4-dichloro-phenyl)-2-methyl-acryloylamino]-benzoic acid; or pharmaceutical salts thereof.

It is understood that the definition of compounds of formula (I), when $R_1$, $R_2$, $R_3$, $R_4$, $R_5$, $R_6$, $R_7$, $R_8$, $R_9$, and $R_{10}$ contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R_1$, $R_2$, $R_3$, $R_4$, $R_5$, $R_6$, $R_8$, $R_9$, and $R_{10}$ contains a carboxyl group, salts of the compounds in this invention may be formed with bases such as alkali metals (Na, K, Li) or alkaline earth metals (Ca or Mg).

"Alkyl" as used herein means a branched or straight chain having from 1 to 12 carbon atoms and more preferably from 1 to 6 carbon atoms. Exemplary alkyl groups include methyl, ethyl, propyl, isopropyl, butyl, isobutyl, t-butyl, pentyl and hexyl.

"Alkenyl" as used herein means a branched or straight chain having from 2 to 12 carbon atoms and more preferably from 1 to 6 carbon atoms, the chain containing at least one carbon-carbon double bond. Alkenyl, may be used synonymously with the term olefin and includes alkylidenes. Exemplary alkenyl groups include ethylene, propylene and isobutylene.

"Alkoxy" as used herein means an alkyl-O group in which the alkyl group is as previously described. Exemplary alkoxy groups include methoxy, ethoxy, n-propoxy, i-propoxy, n-butoxy, and t-butoxy.

"Haloalkyl" as used herein refers to an alkyl group, as defined above, in which one or more hydrogen atoms are replaced with a halogen. Perhaloalkyl refers to alkyl groups in which each of the hydrogens are replaced with halogen atoms. Exemplary haloalkyl groups include chloromethyl, dibromomethyl, and the perhaloalkyl, trifluoromethyl.

"Aryl" as used herein means mono or bicyclic aromatic ring having from 6 to 12 carbon atoms. Monocyclic rings preferably have 6 or 7 members and bicyclic rings preferably have 8, 9 or 10 membered ring structures. Exemplary aryl groups include phenyl and naphthyl. The aryl group may be substituted with one or more substituents. Substituted aryl groups preferably have one to three substituents which may include alkyl, alkoxy, perhaloalkyl, halogen, nitro, amino, carboxy, carboxyalkyl, alkylamino, and dialkylamino.

"Aralkyl" as used herein means an aryl-alkyl group in which the aryl and alkyl group are previously defined. Exemplary aralkyl groups include benzyl and phenethyl.

"Alkanoyl" as used herein refers to —C(O)R where R is alkyl as previously defined.

"Aryloyl" as used herein refers to —C(O)R where R is aryl as previously defined.

"Aralkanoyl" as used herein refers to —C(O)R where R is aralkyl as previously defined.

"Carboxamido" as used herein refers to —CONH₂.

"Sulfamoyl" as used herein refers to —SONH₂.

"Sulfamido" as used herein refers to —RSONH₂. Thus, alkyl-, aryl-, and aralkylsulfamido refer to groups in which the R is alkyl, aryl or aralkyl as previously defined.

"Sulfinyl" as used herein refers to the radical —SOR. Thus, alkyl-, aryl-, and aralkylsulfinyl refer to groups in which the R is alkyl, aryl or aralkyl, as previously defined.

"Sulfonyl" as used herein refers to the radical —SO₂R. Thus, alkyl-, aryl-, and aralkylsulfonyl refer to groups in which the R is alkyl, aryl or aralkyl, as previously defined.

"Halogen", as used herein means chloro, fluoro, bromo and iodo.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, perhaloalkoxy refers to an alkoxy group, as defined above, in which each hydrogen atoms of the alkyl group has been replaced by a halogen.

The present invention also provides a process for the preparation of compounds of formula (I). Methods of preparation are shown in Schemes 1 and 2. Starting materials (II) and (III) are allowed to react (Scheme 1) in the presence of an appropriate base such as, but not limited to, n-butyllithium, sec-butyllithium, tert-butyllithium, lithium diisopropylamimide, lithium, potassium or sodium hexamethyldisilazide, or lithium, potassium or sodium tetramethylpiperadide,

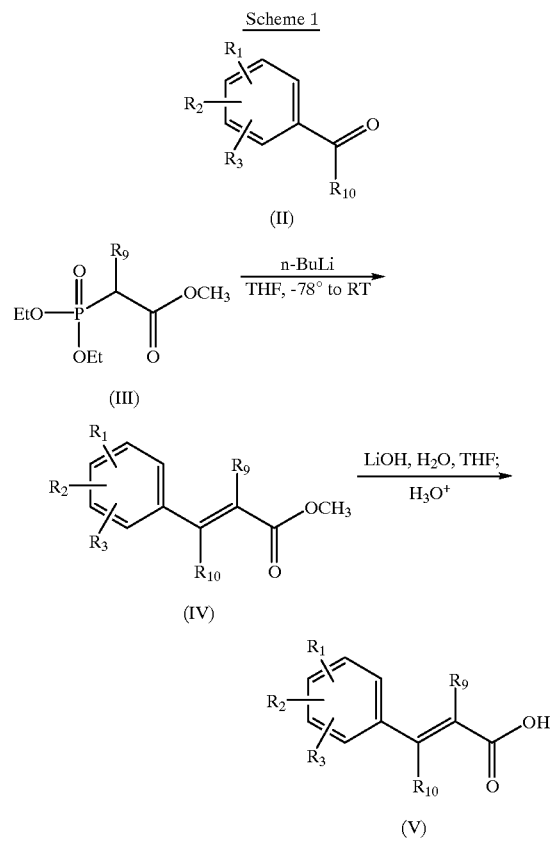

to give condensation product (IV), wherein $R_1$, $R_2$, $R_3$, $R_9$, and $R10_9$, respectively, are as defined hereinbefore, or a group of atoms convertible thereto. Saponification of the ester provides the intermediate carboxylic acid (V).

Carboxylic acid intermediate (V) can subsequently be coupled (Scheme 2) to the amine of an appropriately derivatized anthranilic acid of the formula (VI) or (VII) utilizing one of the following established coupling procedures (Method A: (COCl)₂, cat. DMF, CH₂Cl₂, then add the neat acid chloride to a solution of anthranilic acid in sodium hydroxide; Method B: diisopropylcarbodiimide, DMAP, CH₂Cl₂, then add methyl anthranilate; or Method C: (COCl)₂, cat. DMF, CH₂Cl₂, or SOCl₂ followed by treatment of the neat acid chloride with triethylamine and methyl anthranilate) to afford amides of formula (Ia) or (Ib). If the esters of (VI) or (VII) are used, then final saponification affords the free acids ($R_{15}$=H).

Scheme 2

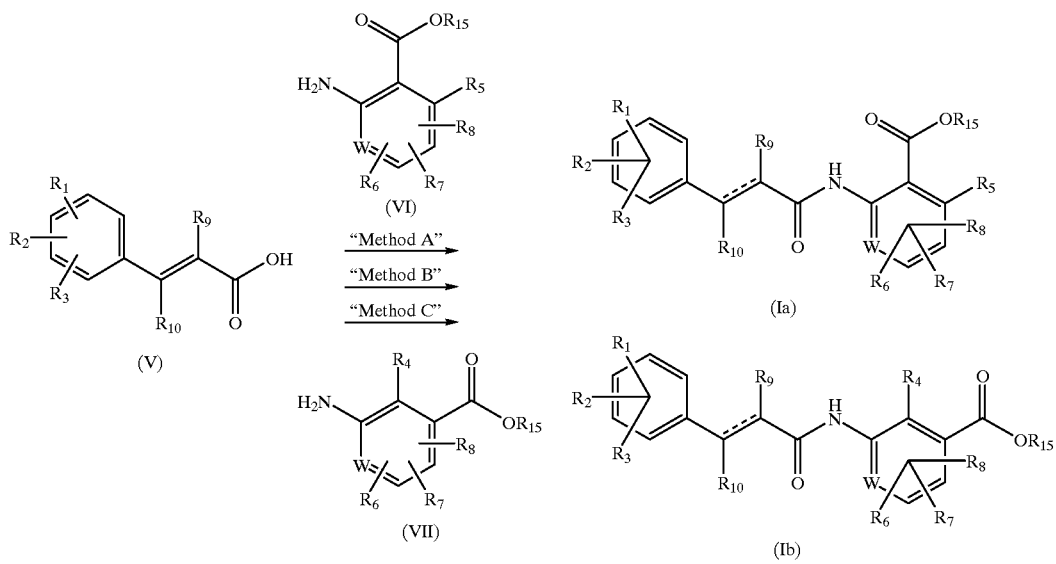

In addition to $CH_2Cl_2$, the reactions mentioned above may be carried out in aprotic solvents such as diethyl ether, dichloroethane, dioxane or THF at low to ambient temperatures. Where sodium hydroxide is used as a base, other inorganic bases which may also suffice are lithium hydroxide or potassium hydroxide, etc. Likewise, triethylamine may be optionally substituted with any trialkylamine.

Compounds of Formula (I) may also be prepared using solid phase synthesis.

As mentioned previously, the compounds of formula (I), and their pharmaceutically acceptable salts have been found to relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of formula (I) are active as potassium channel activators which render them useful for treatment of peripheral vascular disease, congestive heart failure, stroke, anxiety, cerebral anoxia and other neurodegenerative disorders. Moreover, compounds of formula (I) may also be active as chloride channel blockers, which again renders them useful for treatment of the above stated disorders.

Compounds of the present invention are characterized by their potent smooth muscle relaxing properties in vitro. The compounds of this invention exert their smooth muscle relaxatory activity via activation of potassium channels and/or blocking of chloride channels. Members of this series are expected to be active in vivo as evidenced by in vivo activity shown in a model of rat bladder hypertrophy (Table II). In addition, the compounds of the present invention are unique in that they possess intrinsic selectivity for bladder tissue over vascular tissue as demonstrated by bladder/aorta $IC_{50}$ ratios (Table 1). Comparative compound, Tranilast® was shown not to be a potent or bladder selective smooth muscle relaxant.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may also be adapted for other modes of administration, for example, parenteral administration for patients suffering from heart failure or intransally for patients suffering from asthma.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLES

Example 1

(E)-2-[2-Methyl-3-(4-trifluoromethyl-phenyl)-acryloylamino]-benzoic acid lithium salt Step 1) Preparation of (E)-[2-methyl-3-(4-trifluoromethylphenyl)]-2-propenoic acid methyl ester To a solution of 2.5 M n-butyllithium (25.3 mL, 63.2 mmol) in hexanes and THF (50 mL) at −25° C. was added via syringe pump over 22 min methyl 2-diethylphosphonopropionate (13.7 mL, 68.9 mmol). The resultant mixture was stirred an additional 0.5 h at −25° C., whereupon it was chilled to −80° C. To this was added via syringe pump over 30 min α,α,α-trifluoro-p-tolualdehyde (10.0 g, 57.4 mmol) as a solution in THF (15 mL). Upon completed addition, the cooling bath was allowed to warm very slowly to 10° C. over a period of 12 h. The reaction mixture was subsequently quenched with MeOH (1.0 mL), and all volatiles were removed by rotary evaporation. The residue was then partitioned between ether (250 mL) and water (100 mL). The organic phase was washed with brine (100 mL) and dried over $MgSO_4$. Submission of the crude product to flash chromatography (elution with 2% ether-hexanes) afforded upon concentration 11.32 g (81%) of a white solid: $^1$H NMR (DMSO-$d_6$) δ7.66–7.79 (m, 5 H), 3.77 (s, 3 H), 2.04 (d, 3 H).

Step 2) Preparation of (E)-[2-methyl-3-(4-trifluoromethylphenyl)]-2-propenoic acid To a homogeneous solution of the above methyl ester (11.2 g, 45.9 mmol) in THF (320 mL) at RT was added 1.00 N LiOH (138 mL, 138 mmol). The resulting biphasic mixture was stirred vigorously for 16 h, whereupon all volatiles were removed by rotary evaporation. The leftover aqueous solution was washed with ether (3×100 mL), acidified to pH 2 with concentrated HCl (13.4 mL), and partitioned with ether (300 mL). The aqueous phase was then saturated with solid $NH_4Cl$, and extracted again (2×150 mL). The combined organic extracts were dried over $MgSO_4$, treated with Norite, filtered through celite, and concentrated to a solid. Trituration with ether-hexanes followed by filtration and drying in vacuo yielded 8.60 g (81%) of a white solid: $^1$H NMR (DMSO-$d_6$) δ12.69 (s, 1 H), 7.62–7.79 (m, 5 H), 2.01 (d, 3 H).

Step 3) Preparation of (E)-2-[2-Methyl-3-(4-trifluoromethyl-phenyl)-acryloylamino]-benzoic acid To a heterogeneous mixture of the above carboxylic acid (1.00 g, 4.34 mmol) and anhydrous DMF (2 drops) in anhydrous $CH_2Cl_2$ (5 mL) at 0° C. was added dropwise oxalyl chloride (760 μL, 8.69 mmol). The resultant mixture was warmed to RT and stirred for 2.5 h, whereupon it was concentrated to a heterogeneous yellow mixture and purged of excess oxalyl chloride in vacuo. The acid chloride was then added to a homogeneous solution of anthranilic acid (1.19 g, 8.69 mmol) in 2.5 N aqueous NaOH (6.95 mL, 17.4 mmol) at 5° C., resulting in the instantaneous formation of a white precipitate. The reaction mixture was then warmed to RT, whereupon it was diluted with a minimal amount of water to facilitate stirring, which was continued for an additional 1.5 h. The mixture was acidified to pH 2 by addition of concentrated HCl (1.63 mL), diluted with 2.0 N HCl, and stirred for 1.5 h. Filtration of the suspension followed by washing with water, air drying and subsequent recrystallization from MeOH afforded 568 mg (37%) of a highly crystalline white solid: mp 207–208° C.; $^1$H NMR (DMSO-$d_6$) δ13.76 (br s, 1 H), 8.68 (dd, 1 H), 8.04 (dd, 1 H), 7.56–7.81 (m, 6 H), 7.19 (ddd, 1 H), 2.18 (d, 1 H); IR (KBr) 3396, 3116, 2722, 2651, 1674, 1607, 1584, 1534, 1471, 1452, 1411, 1382, 1328, 1291, 1260, 1198, 1166, 1118, 1107, 1068, 1016, 996, 903, 824, 757, 696, 664 $cm^{-1}$; MS (m/z) 349 [$M^+$].

Elemental analysis for $C_{18}H_{14}F_3NO_3$:
Calc'd: C, 61.89; H, 4.04; N, 4.01.
Found: C, 61.87; H, 4.04; N, 4.01.

Step 4) Preparation of (E)-2-[2-Methyl-3-(4-trifluoromethyl-phenyl)-acryloylamino]-benzoic acid lithium salt To a solid mixture of the above carboxylic acid (4.907 g, 14.05 mmol) and lithium hydride dust (111.7 mg, 14.05 mmol) under an atmosphere of $N_2$ was added THF (90 mL, distilled from sodium benzophenone ketyl), at RT. The heterogeneous mixture was heated at reflux for 12 h, producing a copious white precipitate, whereupon it was cooled to RT, diluted with THF (1000 mL), filtered through celite, and concentrated to a white solid. The solid was then triturated with ether (500 mL, distilled from sodium benzophenone ketyl) for 12 h, producing a fine white suspension, filtered over an atmosphere of $N_2$, washed with ether (500 mL), and finally dried under high vacuum at 80° C. affording 4.2655 g (85%) of a white powder: mp 321.5–322.3° C.(dec); $^1$H NMR (DMSO-$d_6$) δ15.21 (s, 1 H), 8.59 (dd, 1 H), 8.00 (dd, 1 H), 7.71 (ABq, 4 H), 7.51 (s, 1 H), 7.28 (ddd, 1 H), 6.95 (ddd, 1 H), 3.35 (s, 3 H); IR (KBr) 3354, 3127, 1647, 1623, 1598, 1527, 1453, 1388, 1325, 1251, 1191, 1127, 1068, 1018, 998, 915, 862, 830, 763, 704 $cm^{-1}$; MS (m/z) 348 [(M–Li)$^-$].

Elemental analysis for $C_{18}H_{13}F_3LiNO_3$:
Calc'd: C, 60.85; H, 3.70; N, 3.94.
Found: C, 60.34; H, 3.50; N, 3.80.

Example 2

2-[3-(4-Trifluoromethyl-phenyl)-propionylamino]-benzoic acid

A mixture of 3-(4-trifluoromethylphenyl)-propionic acid (2.14 g, 10.0 mmol) and thionyl chloride (0.80 mL, 11.0 mmol) was heated to reflux in benzene (100 mL) until all starting material was consumed as indicated by TLC. This mixture was concentrated via rotary evaporation providing the crude acid chloride, which was combined with anthranilic acid (1.37 g, 10.0 mmol) in dimethylacetamide (100 mL) and then refluxed for 12 h. The reaction mixture was cooled to RT, and partitioned between water and ether. The organic phase was dried over $Na_2SO_4$, concentrated, triturated repeatedly with MeOH, then dried to yield 3.40 g (100%) of a white solid: mp 169–171° C.; $^1$H NMR (DMSO-$d_6$) δ13.4–13.7 (br s, 1 H), 11.12 (s, 1 H), 8.45 (dd, 1 H), 7.63 (d, 2 H), 7.57 (ddd, 1 H), 7.50 (d, 2 H), 7.13 (ddd, 1 H), 3.03 (t, 2 H), 2.77 (t, 2 H); IR (KBr) 3124, 3036, 2983, 1711, 1661, 1609, 1585, 1335, 1315, 1224, 1192, 1163, 1145, 1122, 1107, 1070, 791, 760 $cm^{-1}$; MS (m/z) 379 [$M^+$].

Elemental analysis for $C_{17}H_{14}F_3NO_3$:
Calc'd: C, 60.54; H, 4.18; N, 4.15.
Found: C, 60.27; H, 4.26; N, 4.19.

Example 3

(E)-2-[3-(4-Bromo-phenyl)-acryloylamino]-benzoic acid

Step 1) Preparation of (E)-2-[3-(4-Bromo-phenyl)-acryloylamino]-benzoic acid methyl ester To a heterogeneous mixture of 4-bromocinammic acid (2.25 g, 9.91 mmol) and DMAP (121 mg, 0.991 mmol) in $CH_2Cl_2$ at 0° C. was added 1,3-diisopropyl-carbodimide (1.55 mL, 9.91 mmol). The resultant mixture was stirred for 30 min, at which point was added methyl anthranilate (1.92 mL, 14.9 mmol). The reaction mixture was kept at 0° C. for 10 min, and then allowed to warm to RT whereupon it was stirred for 72 h. The reaction mixture was then diluted with EtOAc (200 mL) and succesively partitioned with 2.0 N HCl (50 mL), water (50 mL), saturated $NaHCO_3$ (50 mL), and finally brine (50 mL). The organic phase was dried over $MgSO_4$, treated with Norite, filtered through celite, and concentrated to a solid. Trituration with ether-hexanes, followed by filtration, washing with 20% ether-petroleum ether and drying in vacuo afforded 2.81 g of crude white solid. Recrystalization from MeOH provided 1.59 g (45%) of analytically pure material as white crystalline plates: $^1$H NMR (DMSO-d$_6$) δ10.83 (s, 1 H), 8.39 (dd, 1 H), 7.94 (dd, 1 H), 7.71–7.56 (m, 6 H), 7.21 (ddd, 1 H), 6.97 (d, 1 H), 3.87 (s, 1 H).

Step 2) (E)-2-[3-(4-Bromo-phenyl)-acryloylamino]-benzoic acid

In a manner similar to Example 1, Step 2 was prepared the title compound (781 mg, 52%): mp 215–216° C.; 1H NMR (DMSO-d$_6$) δ13.52 (br s, 1 H), 11.33 (s, 1 H), 8.59 (dd, 1 H), 8.01 (dd, 1 H), 7.58–7.72 (m, 6H), 7.18 (ddd, 1 H), 6.94 (d, 1 H); IR (KBr) 3331, 3123, 3072, 1705, 1670, 1626, 1606, 1583, 1526, 1487, 1449, 1413, 1402, 1389, 1261, 1224, 1146, 1071, 966, 882, 816, 750, 656 cm$^{-1}$; MS (m/z) 345/347 [M$^+$].

Elemental analysis for $C_{16}H_{12}BrNO_3$:
Calc'd: C, 55.51; H, 3.49; N, 4.04.
Found: C, 55.10; H, 3.50; N, 4.10.

Example 4

(E)-2-[3[(4-Trifluoromethyl-phenyl)-acryloylamino]-benzoic acid

A mixture of trans-4-(trifluoromethyl)cinnamic acid (2.02 g, 9.34 mmol), thionyl chloride (2.0 mL, 27.4 mmol), and methyl anthranilate (2.4 mL, 13.6 mmol) were refluxed in benzene (100 mL) for 96 h. Concentration in vacuo, followed by crystallization with MeOH afforded, upon filtration, 1.3 g (40%) of the intermediate methyl ester. To a solution of this intermediate (873 mg, 2.50 mmol) in THF (25 mL) was added 1N NaOH (7.5 mL, 7.5 mmol). The resulting mixture was stirred until hydrolysis was completed, whereupon it was acidified to pH 3 with HCl, and stirred for 30 min. The organic phase was separated, washed with brine, dried over MgSO$_4$, and then concentrated in vacuo yielding 500 mg (60%) of a white solid: mp 222–224° C.; $^1$H NMR (DMSO-d$_6$) δ13.3–13.9 (br s, 1 H), 11.36 (s, 1 H), 8.59 (dd, 1 H), 8.01 (dd, 1 H), 7.97 (d, 2 H), 7.78 (d, 2 H), 7.69 (d, 1 H), 7.63 (ddd, 1 H), 7.20 (ddd, 1 H); IR (KBr) 3329, 3063, 2877, 1674, 1628, 1606, 1585, 1530, 1472, 1451, 1414, 1329, 1299, 1262, 1214, 1165, 1118, 1110, 1068, 972, 893, 831, 756, 657 cm$^{-1}$; MS (m/z) 335 [M$^+$].

Elemental analysis for $C_{17}H_{12}F_3NO_3$:
Calc'd: C, 60.90; H, 3.61; N, 4.18.
Found: C, 60.50; H, 3.55; N, 4.21.

Example 5

(E)-2-[3[(4-Trifluoromethyl-phenyl)-acryloylamino]-benzoic acid lithium salt hemihydrate In a manner similar to Step 4 of Example 1 was prepared the title compound (64%) from the above carboxylic acid: mp>340° C. (dec); $^1$H NMR (DMSO-d$_6$) δ15.03 (s, 1 H), 8.56 (dd, 1 H), 8.00 (dd, 1 H), 7.84 (ABq, 4 H), 7.61 (d, 1 H), 7.28 (ddd, 1 H), 6.96 (ddd, 1 H), 6.84 (d, 1 H); IR (KBr) 3715, 3678, 3423, 3264, 3060, 1693, 1620, 1587, 1512, 1415, 1384, 1294, 1166, 1111, 1067, 976, 828, 759 cm$^{-1}$; MS (m/z) 334 [(M−Li)$^-$].

Elemental analysis for $C_{17}H_{11}F_3NO_3Li·0.5\ H_2O$:
Calc'd: C, 59.84; H, 3.26; N, 4.11.
Found: C, 58.78; H, 3.22; N, 4.06.

Example 6

2-[3-(4-Trifluoromethyl-phenyl)-but-3-enoylamino]-benzoic acid

Step 1) Preparation of (E)-[3-(4-trifluoromethyl-phenyl)]-but-2-enoic acid methyl ester In a manner similar to Step 1 of Example 1 was prepared the title intermediate (46%) from 4-(trifluoromethyl-phenyl)-acetophenone: $^1$H NMR (DMSO-d$_6$) δ7.77 (ABq, 4 H), 6.24 (q, 1 H), 3.68 (s, 3 H), 2.52 (d, 3 H).

Step 2) Preparation of (E)-[3-(4-trifluoromethyl-phenyl)]-but-2-enoic acid

In a manner similar to Step 2 of Example 1 was prepared the title intermediate (82%) as a white solid: $^1$H NMR (DMSO-d$_6$) δ12.42 (s, 1 H), 7.75 (s, 4 H), 6.17 (q, 1 H).

Step 3) Preparation of 2-[3-(4-trifluoromethyl-phenyl)-but-3-enoylamino]-benzoic acid methyl ester To a homogeneous solution of the above carboxylic acid (1.75 g, 7.60 mmol), DMAP (186 mg, 1.52 mmol) and methyl anthranilate (1.97 mL, 15.2 mmol) in CH$_2$Cl$_2$ was added dropwise at 0° C. diisopropylcarbodiimide (1.19 mL, 7.60 mmol). The resultant yellow mixture was stirred at 0° C. for 1 h, then warmed to RT and stirred for an additional 48 h. The reaction mixture was diluted with ether (400 mL), extracted consecutively with water (3×200 mL) and brine (200 mL). The organic phase was dried over MgSO$_4$, treated with 1.0 M ethereal HCl (8.0 mL, 8.0 mmol), filtered through a short pad of SiO$_2$, then concentrated to an oily residue which was submitted to flash chromatography (elution with 20% ether-hexanes) affording 1.58 g (57%) as a white solid: $^1$H NMR (DMSO-d$_6$) δ10.75 (s, 1 H), 8.26 (dd, 1 H), 7.88 (dd, 1 H), 7.73 (ABq, 4 H), 7.56 (ddd, 1 H), 7.15 (ddd, 1 H), 5.85 (s, 1 H), 5.55 (s, 1 H), 3.81 (s, 3 H), 3.75 (s, 2 H).

Step 4) Preparation of 2-[3-(4-Trifluoromethyl-phenyl)-but-3-enoylamino]-benzoic acid The above ester was saponified as described in Step 2 of Example 1 to give a mixture of olefin isomers. To this mixture (325 mg, 0.930 mmol) was added ethereal 1.0 N HCl (30 mL, 30 mmol) at RT. The resultant homogeneous solution was stirred for 20 min, then diluted to 200 mL with petroleum ether, resulting in the formation of a copious precipitate. This mixture was stirred 1 h, then filtered, and dried under high vacuum at 60° C. to afford 218.7 mg (67%) of the terminal olefinic isomer as a white solid: mp 174–175° C.; $^1$H NMR (DMSO-d$_6$) δ13.53 (br s, 1 H), 11.31 (s, 1 H), 8.45 (dd, 1 H), 7.93 (dd, 1 H), 7.72 (ABq, 4 H), 7.53 (ddd, 1 H), 7.11 (ddd, 1 H), 5.86 (s, 1 H), 5.57 (s, 1 H), 3.75 (s, 3 H); IR (KBr) 3183, 2993, 2651, 1694, 1635, 1582, 1511, 1451, 1406, 1325, 1235, 1176, 1064, 1014, 983, 940, 863, 797, 751, 727, 695 cm$^{-1}$; MS (m/z) 349 [M$^+$].

Elemental analysis for $C_{18}H_{14}F_3NO_3$:
Calc'd: C, 61.89; H, 4.04; N, 4.01.
Found: C, 61.81; H, 3.94; N, 4.22.

Example 7

(E)-2-[3-(4-Trifluoromethyl-phenyl)-but-2-enoylamino]-benzoic acid sodium salt

In a manner similar to Step 3 of Example 1 was prepared the title compound from (E)-[3-(4-trifluoromethyl-phenyl)]-but-2-enoic acid and anthranilic acid. The final workup entailed treatment of the reaction mixture with sufficient 2.0 N HCl to bring the medium to neutrality. Following recrystallization from MeOH, 110 mg (8%) of the sodium salt was isolated as a hygroscopic white solid: mp 325–328° C.; $^1$H NMR (DMSO-d$_6$) δ14.68 (s, 1 H), 8.54 (dd, 1 H), 7.98 (dd, 1 H), 7.77 (ABq, 4 H), 7.28 (ddd, 1 H), 6.95 (ddd, 1 H), 6.27 (d, 1 H), 2.57 (d, 3H); IR (KBr) 3439, 3236, 3157, 3024, 1665, 1618, 1589, 1441, 1383, 1326, 1304, 1168, 1120, 1080, 1066, 1014, 836, 760 cm$^{-1}$; MS (m/z) 349 [M+].

Elemental Analysis for $C_{18}H_{13}F_3NO_3Na$:

Calc'd: C, 58.23; H, 3.53; N, 3.77.

Found: C, 57.38; H, 3.41; N, 3.72.

Example 8

(E)-5-Chloro-2-[2-methyl-3-(4--trifluoromethyl-phenyl)-acryloylamino-benzoic acid In a manner similar to Step 3 of Example 1 was prepared the title compound (47%) from (E)-3-[4-trifluoromethylphenyl]-2-propenoic acid and 4-chloroanthranilic acid: mp 225.3–225.8° C.; $^1$H NMR (DMSO-d$_6$) δ11.79 (s, 1 H), 8.68 (d, 1 H), 7.96 (d, 1 H), 7.73 (ABq, 4 H), 7.71 (dd, 1 H), 7.56 (s, 1 H), 2.17 (d, 3 H); IR (KBr) 3132, 1698, 1662, 1611, 1583, 1519, 1381, 1330, 1293, 1167, 1114, 1070, 1000, 847, 833, 688 cm$^{-1}$; MS (m/z) 383/385 [M+].

Elemental analysis for $C_{18}H_{13}ClF_3NO_3$:

Calc'd: C, 56.34; H, 3.41; N, 3.65.

Found: C, 56.21; H, 3.20; N, 3.71.

Example 9

(E)-5-Chloro-2-[2-methyl-3-(4-trifluoromethyl-phenyl)-acryloylamino]-benzoic acid lithium salt hemihydrate In a manner similar to Step 4 of Example 1 was prepared the title compound (89%) from (E)-5-Chloro-2-[2-methyl-3-(4-trifluoromethyl-phenyl)-acryloylamino-benzoic acid as a hygroscopic white solid: mp 244.9–262° C.; $^1$H NMR (DMSO-d$_6$) δ15.10 (s, 1 H), 8.62 (d, 1 H), 7.80 (ABq, 4 H), 7.50 (s, 1 H), 7.33 (dd, 1 H), 2.15 (d, 3 H); IR (KBr) 3750, 3413, 3124, 1657, 1616, 1583, 1512, 1441, 1412, 1374, 1325, 1251, 1204, 1167, 1126, 1068, 999, 830, 736, 697 cm$^{-1}$; MS (m/z) 396 [(M+H+Li)+].

Elemental analysis for $C_{18}H_{12}ClF_3NO_3Li.0.5\ H_2O$:

Calc'd: C, 55.43; H, 3.08; N, 3.59.

Found: C, 54.15; H, 3.12; N, 3.51.

Example 10

(E)-4-Chloro-2-[2-methyl-3-(4-trifluoromethyl-phenyl)-acryloylamino]-benzoic acid In a manner similar to Step 3 of Example 1 was prepared the title compound (36%) from (E)-3-[4-trifluoromethylphenyl]-2-propenoic acid and 5-chloroanthranilic acid: mp 228.4–229.0° C.; $^1$H NMR (DMSO-d$_6$) δ11.97 (s, 1 H), 8.78 (d, 1 H), 8.03 (d, 1 H), 7.74 (ABq, 4 H), 7.57 (s, 1 H), 7.26 (dd, 1 H), 2.18 (d, 3 H); IR (KBr) 3420, 3225, 3010, 2930, 2600, 1710, 1660, 1615, 1600, 1420, 1345, 1295, 1115, 1075, 1000, 915, 850, 785, 725, 690 cm$^{-1}$; MS (m/z) 383/385 [M+].

Elemental analysis for $C_{18}H_{13}ClF_3NO_3$:

Calc'd: C, 56.34; H, 3.42; N, 3.65.

Found: C, 55.94; H, 3.23; N, 3.86.

Example 11

(E)-4-Chloro-2-[2-methyl-3-(4-trifluoromethyl-phenyl)-acryloylamino]-benzoic acid lithium salt hemihydrate In a manner similar to Step 4 of Example 1 was prepared the title compound (79%) from (E)-4-Chloro-2-[2-methyl-3-(4-trifluoromethyl-phenyl)-acryloylamino]-benzoic acid as a hygroscopic white solid: mp 320.9–321.4° C. (dec); $^1$H NMR (DMSO-d$_6$) δ8.68 (d, 1 H), 8.00 (d, 1 H), 7.72 (ABq, 4 H), 7.52 (s, 1 H), 7.01 (dd, 1 H), 2.16 (d, 3 H); IR (KBr) 3662, 3405, 3103, 2994, 2647, 1659, 1618, 1573, 1512, 1440, 1373, 1327, 1242, 1167, 1110, 1068, 1000, 914, 847, 769, 693 cm$^{-1}$; MS (m/z) 396 [(M+Li)+], 390, [(M+H)+].

Elemental analysis for $C_{18}H_{12}ClF_3NO_3Li.0.5\ H_2O$:

Calc'd: C, 55.48; H, 3.11; N, 3.60.

Found: C, 54.14; H, 3.06; N, 3.42.

Example 12

(E)-2-[2-Methyl-3-(4-trifluoromethyl-phenyl)-acryloylamino]-nicotinic acid

Step 1) Preparation of (E)-2-[2-Methyl-3-(4-trifluoromethyl-phenyl)-acryloylamino]-nicotinic acid methyl ester To a solution of 2-aminonicotinic acid methyl ester (0.50 g, 3.26 mmol) and triethylamine (910 μL, 6.52 mmol) in CH$_2$Cl$_2$ at 0° C. was added via cannula (E)-3-[4-trifluoromethylphenyl]-2-propenoyl chloride (810 mg, 3.26 mmol), prepared in a manner identical to Step 3 of Example 1, as a solution in CH$_2$Cl$_2$ (5.0 mL). Upon completed addition, the reaction mixture was allowed to warm to RT and stir for 2 h, whereupon it was quenched with water (20 mL) and saturated NaHCO$_3$ (20 mL), then partitioned with EtOAc (20 mL). The aqueous phase was further extracted with EtOAc (3×20 mL), and the combined organic extracts were dried over MgSO$_4$, treated with Norite, concentrated and submitted to flash chromatography (elution with 75% EtOAc-hexanes) to afford 412 mg (35%) of a white solid.

Step 2) Preparation of (E)-2-[2-Methyl-3-(4-trifluoromethyl-phenyl)-acryloylamino]-nicotinic acid In a manner similar to Step 2 of Example 1 was prepared the title compound (61%) from the above methyl ester: mp 203.8–2.4.4° C.; $^1$H NMR (DMSO-d$_6$) δ11.20 (br s, 1 H), 8.54 (dd, 1 H), 8.21 (dd, 1 H), 7.73 (ABq, 4 H), 7.45 (s, 1 H), 7.28 (dd, 1 H), 2.11 (d, 3 H); IR (KBr) 3301, 3079, 2994, 1686, 1607, 1560, 1454, 1411, 1387, 1261, 1203, 1189, 1168, 1148, 1047, 1016, 997, 892, 850, 777, 682 cm$^{-1}$; MS (m/z) 350 [M+].

Elemental analysis for $C_{17}H_{13}F_3N_2O_3$:

Calc'd: C, 58.29; H, 3.74; N, 8.00.

Found: C, 57.45; H, 3.56; N, 7.76.

Example 13

(E)-5-Methoxy-2-[2-methyl-3-(4-trifluoromethyl-phenyl)-acryloylamino]-benzoic acid In a manner similar to to Step 3 of Example 1 was prepared the title compound (39%) from (E)-3-[4-trifluoromethylphenyl]-2-propenoic acid and 4-methoxy-anthranilic acid: mp 207.2–208.0° C.; $^1$H NMR (DMSO-d$_6$) δ13.80 (br s, 1 H), 11.54 (s, 1 H), 8.56 (d, 1 H), 7.73 (ABq, 4 H), 7.53 (s, 1 H), 7.50 (d, 1 H), 7.26 (dd, 1 H), 3.78 (s, 3 H), 2.17 (d, 3 H); IR (KBr) 3310, 3212, 3142, 3105, 2947, 2858, 1697, 1607, 1554, 1502, 1452, 1411, 1382, 1358, 1335, 1246, 1172, 1141, 1121, 1063, 855, 810, 751, 737, 691 cm$^{-1}$; MS (m/z) 379 [M+].

Elemental analysis for $C_{19}H_{16}F_3NO_4$:

Calc'd: C, 60.16; H, 4.25; N, 3.69.

Found: C, 60.31; H, 4.09; N, 3.65.

Example 14

(E)-2-[2-Methyl-3-(4-trifluoromethyl-phenyl)-acryloylamino]-benzoic acid diethylcarbamoylmethyl ester Step 1) Preparation of (E)-2-[2-Methyl-3-(4-trifluoromethyl-phenyl)-acryloylamino]-benzoic acid sodium salt In a manner similar to Step 4 of Example 1 (lithium hydride replaced by sodium hydride) was prepared the title intermediate (91%) from the corresponding carboxylic acid. Step 2) Preparation of (E)-2-[2-Methyl-3-(4-trifluoromethyl-phenyl)-acryloylamino]-benzoic acid diethylcarbamoylmethyl ester To a homogeneous solution of the above carboxylate sodium salt (894 mg, 2.41 mmol) and sodium iodide (36 mg, 0.24 mmol) in DMF at RT under an inert atmosphere of $N_2$ was added dropwise N,N-diethyl-2-chloroacetamide (397 µL, 2.89 mmol). Upon completed addition, the reaction mixture was heated to 50° C. and stirred for 12 h, whereupon it was quenched with water (25 mL), then partitioned with EtOAc (50 mL). The aqueous phase was extracted again with EtOAc (50 mL); the combined organic phases were washed with 2% $NaHCO_3$ (2×25 mL), then diluted with hexanes (25 mL), and washed consecutively with water (3×25 mL) followed by brine (25 mL). Drying with $MgSO_4$, followed by concentration and recrystallization from ether-petroleum ether afforded 898 mg (74%) of a white solid: mp 76.4–77.2° C.; $^1$H NMR (CDCl$_3$) δ11.46 (s, 1 H), 7.58–7.63 (m, 2 H), 7.57 (ABq, 4 H), 7.14 (ddd, 1 H), 4.99 (s, 2 H), 3.37 (dq, 4 H), 2.24 (d, 3 H), 1.21 (dt, 6 H); IR (KBr); MS (m/z).

Elemental analysis for $C_{24}H_{25}F_3N_2O_4$:
Calc'd: C, 62.33; H, 5.45; N, 6.06.
Found: C, 62.09, H, 5.30; N, 6.05.

Solid Phase Synthesis of Examples 15 through 264

To a suspension of Wang resin (0.7 g, 0.52 mmol) and triphenylphosphine (0.409 g, 1.56 mmol, 3 eq) in dichloromethane (4 ml) was added N-chlorosuccinimide (0.394 g, 1.72 mmol, 3.3 eq) at 0° C. The reaction was continued at 0° C. for 5 hours and at room temperature for 10 hours. Then the solvent was removed by filtration and the resin was washed with dichloromethane (4×8 ml). Anthranilic acid, or appropriately substituted 1,2 or 1,3 aminobenzoic acid (5 eq), cesium carbonate (0.847 g, 2.6 mmol, 5 eq) and dimethylformamide (DMF) (6 ml) were mixed with the above resin. After 60 hours of reaction, the solvent was filtrated, the resin was washed with water (2×5 ml), DMF (4 ml) and $CH_2Cl_2$ (2×4 ml). Dichloromethane (5 ml), appropriately substituted diethylphosphonoacetic acid (3 eq), diisopropyl carbodiimide (0.261 ml, 1.66 mmol, 3.3 eq) and dimethylaminopyridine (DMAP) (10 mg) were reacted with the above resin for 20 h at room temperature. The reaction mixture was filtered, washed with dichloromethane (5×4 ml) and tetrahydrofuran (THF) (5 ml). Lithium chloride (40 mg, 1.5 mmol. 3 eq), 1,8-diazabicyclo[5.4.0]undec-7-ene (DBU) (150 mg, 1.5 mmol, 3 eq) and THF (10 ml) were mixed with the above resin for 1 hour, then appropriately substituted benzaldehyde (3 eq) was introduced at room temperature. After 18 hours, water (10 ml) was added, the solvent was filtrated, then residue was washed with THF-$H_2O$ (1:1, 10 ml), water (10 ml), THF (10 ml), acetone (3×10 ml) and dichloromethane (3×10 ml).

The above resin was treated with TFA (50% dichloromethane, 6 ml) for 1 hour, the filtrate was evaporated in vacuo to give the crude product. Table A more fully describes the structures of Examples 15 through 264.

| Example | R1 | R2 | R3 | R4 | R5 | R6 | R7 | R8 | R9 | R10 |
|---|---|---|---|---|---|---|---|---|---|---|
| 15 | 2-CH3 | H | H | COOH | H | H | H | H | H | H |
| 16 | 2-CH3 | H | H | COOH | H | H | H | H | CH3 | H |
| 17 | 2-CH3 | H | H | H | COOH | H | H | H | H | H |
| 18 | 2-CH3 | H | H | H | COOH | H | H | H | CH3 | H |
| 19 | 2-CH3 | H | H | COOH | H | H | H | 5-Cl | H | H |
| 20 | 2-CH3 | H | H | COOH | H | H | H | 5-Cl | CH3 | H |
| 21 | 2-CH3 | H | H | H | COOH | H | H | 6-Cl | H | H |
| 22 | 2-CH3 | H | H | H | COOH | H | H | 6-Cl | CH3 | H |
| 23 | 2-CH3 | H | H | COOH | H | H | H | 4-Cl | H | H |
| 24 | 2-CH3 | H | H | COOH | H | H | H | 4-Cl | CH3 | H |
| 25 | 3-CH3 | H | H | COOH | H | H | H | H | H | H |
| 26 | 3-CH3 | H | H | COOH | H | H | H | H | CH3 | H |
| 27 | 3-CH3 | H | H | H | COOH | H | H | H | H | H |
| 28 | 3-CH3 | H | H | H | COOH | H | H | H | CH3 | H |
| 29 | 3-CH3 | H | H | COOH | H | H | H | 5-Cl | H | H |
| 30 | 3-CH3 | H | H | COOH | H | H | H | 5-Cl | CH3 | H |
| 31 | 3-CH3 | H | H | H | COOH | H | H | 6-Cl | H | H |
| 32 | 3-CH3 | H | H | H | COOH | H | H | 6-Cl | CH3 | H |
| 33 | 3-CH3 | H | H | COOH | H | H | H | 4-Cl | H | H |
| 34 | 3-CH3 | H | H | COOH | H | H | H | 4-Cl | CH3 | H |
| 35 | 4-CH3 | H | H | COOH | H | H | H | H | H | H |
| 36 | 4-CH3 | H | H | COOH | H | H | H | H | CH3 | H |
| 37 | 4-CH3 | H | H | H | COOH | H | H | H | H | H |
| 38 | 4-CH3 | H | H | H | COOH | H | H | H | CH3 | H |
| 39 | 4-CH3 | H | H | COOH | H | H | H | 5-CL | H | H |
| 40 | 4-CH3 | H | H | COOH | H | H | H | 5-CL | CH3 | H |
| 41 | 4-CH3 | H | H | H | COOH | H | H | 6-Cl | H | H |
| 42 | 4-CH3 | H | H | H | COOH | H | H | 6-Cl | CH3 | H |
| 43 | 4-CH3 | H | H | COOH | H | H | H | 4-Cl | H | H |
| 44 | 4-CH3 | H | H | COOH | H | H | H | 4-Cl | CH3 | H |
| 45 | 2-F | H | H | COOH | H | H | H | H | H | H |
| 46 | 2-F | H | H | COOH | H | H | H | H | CH3 | H |
| 47 | 2-F | H | H | H | COOH | H | H | H | H | H |
| 48 | 2-F | H | H | H | COOH | H | H | H | CH3 | H |
| 49 | 2-F | H | H | COOH | H | H | H | 5-Cl | H | H |
| 50 | 2-F | H | H | COOH | H | H | H | 5-Cl | CH3 | H |
| 51 | 2-F | H | H | H | COOH | H | H | 6-Cl | H | H |

-continued

| Example | R1 | R2 | R3 | R4 | R5 | R6 | R7 | R8 | R9 | R10 |
|---|---|---|---|---|---|---|---|---|---|---|
| 52 | 2-F | H | H | H | COOH | H | H | 6-Cl | CH3 | H |
| 53 | 2-F | H | H | COOH | H | H | H | 4-Cl | H | H |
| 54 | 2-F | H | H | COOH | H | H | H | 4-Cl | CH3 | H |
| 55 | 3-F | H | H | COOH | H | H | H | H | H | H |
| 56 | 3-F | H | H | COOH | H | H | H | H | CH3 | H |
| 57 | 3-F | H | H | H | COOH | H | H | H | H | H |
| 58 | 3-F | H | H | H | COOH | H | H | H | CH3 | H |
| 59 | 3-F | H | H | COOH | H | H | H | 5-Cl | H | H |
| 60 | 3-F | H | H | COOH | H | H | H | 5-Cl | CH3 | H |
| 61 | 3-F | H | H | H | COOH | H | H | 6-Cl | H | H |
| 62 | 3-F | H | H | H | COOH | H | H | 6-Cl | CH3 | H |
| 63 | 3-F | H | H | COOH | H | H | H | 4-Cl | H | H |
| 64 | 3-F | H | H | COOH | H | H | H | 4-Cl | CH3 | H |
| 65 | 4-F | H | H | COOH | H | H | H | H | H | H |
| 66 | 4-F | H | H | COOH | H | H | H | H | CH3 | H |
| 67 | 4-F | H | H | H | COOH | H | H | H | H | H |
| 68 | 4-F | H | H | H | COOH | H | H | H | CH3 | H |
| 69 | 4-F | H | H | COOH | H | H | H | 5-Cl | H | H |
| 70 | 4-F | H | H | COOH | H | H | H | 5-Cl | CH3 | H |
| 71 | 4-F | H | H | H | COOH | H | H | 6-Cl | H | H |
| 72 | 4-F | H | H | H | COOH | H | H | 6-Cl | CH3 | H |
| 73 | 4-F | H | H | COOH | H | H | H | 4-Cl | H | H |
| 74 | 4-F | H | H | COOH | H | H | H | 4-Cl | CH3 | H |
| 75 | 2-Cl | H | H | COOH | H | H | H | H | H | H |
| 76 | 2-Cl | H | H | COOH | H | H | H | H | CH3 | H |
| 77 | 2-Cl | H | H | H | COOH | H | H | H | H | H |
| 78 | 2-Cl | H | H | H | COOH | H | H | H | CH3 | H |
| 79 | 2-Cl | H | H | COOH | H | H | H | 5-Cl | H | H |
| 80 | 2-Cl | H | H | COOH | H | H | H | 5-Cl | CH3 | H |
| 81 | 2-Cl | H | H | H | COOH | H | H | 6-Cl | H | H |
| 82 | 2-Cl | H | H | H | COOH | H | H | 6-Cl | CH3 | H |
| 83 | 2-Cl | H | H | COOH | H | H | H | 4-Cl | H | H |
| 84 | 2-Cl | H | H | COOH | H | H | H | 4-Cl | CH3 | H |
| 85 | 3-Cl | H | H | COOH | H | H | H | H | H | H |
| 86 | 3-Cl | H | H | COOH | H | H | H | H | CH3 | H |
| 87 | 3-Cl | H | H | H | COOH | H | H | H | H | H |
| 88 | 3-Cl | H | H | H | COOH | H | H | H | CH3 | H |
| 89 | 3-Cl | H | H | COOH | H | H | H | 5-Cl | H | H |
| 90 | 3-Cl | H | H | COOH | H | H | H | 5-Cl | CH3 | H |
| 91 | 3-Cl | H | H | H | COOH | H | H | 6-Cl | H | H |
| 92 | 3-Cl | H | H | H | COOH | H | H | 6-Cl | CH3 | H |
| 93 | 3-Cl | H | H | COOH | H | H | H | 4-Cl | H | H |
| 94 | 3-Cl | H | H | COOH | H | H | H | 4-Cl | CH3 | H |
| 95 | 2-Br | H | H | COOH | H | H | H | H | H | H |
| 96 | 2-Br | H | H | COOH | H | H | H | H | CH3 | H |
| 97 | 2-Br | H | H | H | COOH | H | H | H | H | H |
| 98 | 2-Br | H | H | H | COOH | H | H | H | CH3 | H |
| 99 | 2-Br | H | H | COOH | H | H | H | 5-Cl | H | H |
| 100 | 2-Br | H | H | COOH | H | H | H | 5-Cl | CH3 | H |
| 101 | 2-Br | H | H | H | COOH | H | H | 6-Cl | H | H |
| 102 | 2-Br | H | H | H | COOH | H | H | 6-Cl | CH3 | H |
| 103 | 2-Br | H | H | COOH | H | H | H | 4-Cl | H | H |
| 104 | 2-Br | H | H | COOH | H | H | H | 4-Cl | CH3 | H |
| 105 | 3-Br | H | H | COOH | H | H | H | H | H | H |
| 106 | 3-Br | H | H | COOH | H | H | H | H | CH3 | H |
| 107 | 3-Br | H | H | H | COOH | H | H | H | H | H |
| 108 | 3-Br | H | H | H | COOH | H | H | H | CH3 | H |
| 109 | 3-Br | H | H | COOH | H | H | H | 5-Cl | H | H |
| 110 | 3-Br | H | H | COOH | H | H | H | 5-Cl | CH3 | H |
| 111 | 3-Br | H | H | H | COOH | H | H | 6-Cl | H | H |
| 112 | 3-Br | H | H | H | COOH | H | H | 6-Cl | CH3 | H |
| 113 | 3-Br | H | H | COOH | H | H | H | 4-Cl | H | H |
| 114 | 3-Br | H | H | COOH | H | H | H | 4-Cl | CH3 | H |
| 115 | 2-CF3 | H | H | COOH | H | H | H | H | H | H |
| 116 | 2-CF3 | H | H | COOH | H | H | H | H | CH3 | H |
| 117 | 2-CF3 | H | H | H | COOH | H | H | H | H | H |
| 118 | 2-CF3 | H | H | H | COOH | H | H | H | CH3 | H |
| 119 | 2-CF3 | H | H | COOH | H | H | H | 5-Cl | H | H |
| 120 | 2-CF3 | H | H | COOH | H | H | H | 5-Cl | CH3 | H |
| 121 | 2-CF3 | H | H | H | COOH | H | H | 6-Cl | H | H |
| 122 | 2-CF3 | H | H | H | COOH | H | H | 6-Cl | CH3 | H |
| 123 | 2-CF3 | H | H | COOH | H | H | H | 4-Cl | H | H |
| 124 | 2-CF3 | H | H | COOH | H | H | H | 4-Cl | CH3 | H |
| 125 | 3-CF3 | H | H | COOH | H | H | H | H | H | H |
| 126 | 3-CF3 | H | H | COOH | H | H | H | H | CH3 | H |
| 127 | 3-CF3 | H | H | H | COOH | H | H | H | H | H |
| 128 | 3-CF3 | H | H | H | COOH | H | H | H | CH3 | H |

-continued

| Example | R1 | R2 | R3 | R4 | R5 | R6 | R7 | R8 | R9 | R10 |
|---|---|---|---|---|---|---|---|---|---|---|
| 129 | 3-CF3 | H | H | COOH | H | H | H | 5-Cl | H | H |
| 130 | 3-CF3 | H | H | COOH | H | H | H | 5-Cl | CH3 | H |
| 131 | 3-CF3 | H | H | H | COOH | H | H | 6-Cl | H | H |
| 132 | 3-CF3 | H | H | H | COOH | H | H | 6-Cl | CH3 | H |
| 133 | 3-CF3 | H | H | COOH | H | H | H | 4-Cl | H | H |
| 134 | 3-CF3 | H | H | COOH | H | H | H | 4-Cl | CH3 | H |
| 135 | 4-CF3 | H | H | COOH | H | H | H | H | H | H |
| 136 | 4-CF3 | H | H | COOH | H | H | H | H | CH3 | H |
| 137 | 4-CF3 | H | H | H | COOH | H | H | H | H | H |
| 138 | 4-CF3 | H | H | H | COOH | H | H | H | CH3 | H |
| 139 | 4-CF3 | H | H | COOH | H | H | H | 5-Cl | H | H |
| 140 | 4-CF3 | H | H | COOH | H | H | H | 5-Cl | CH3 | H |
| 141 | 4-CF3 | H | H | H | COOH | H | H | 6-Cl | H | H |
| 142 | 4-CF3 | H | H | H | COOH | H | H | 6-Cl | CH3 | H |
| 143 | 4-CF3 | H | H | COOH | H | H | H | 4-Cl | H | H |
| 144 | 4-CF3 | H | H | COOH | H | H | H | 4-Cl | CH3 | H |
| 145 | H | H | H | COOH | H | H | H | H | H | H |
| 146 | H | H | H | COOH | H | H | H | H | CH3 | H |
| 147 | H | H | H | H | COOH | H | H | H | H | H |
| 148 | H | H | H | H | COOH | H | H | H | CH3 | H |
| 149 | H | H | H | COOH | H | H | H | 5-Cl | H | H |
| 150 | H | H | H | COOH | H | H | H | 5-Cl | CH3 | H |
| 151 | H | H | H | H | COOH | H | H | 6-Cl | H | H |
| 152 | H | H | H | H | COOH | H | H | 6-Cl | CH3 | H |
| 153 | H | H | H | COOH | H | H | H | 4-Cl | H | H |
| 154 | H | H | H | COOH | H | H | H | 4-Cl | CH3 | H |
| 155 | 4-Cl | H | H | COOH | H | H | H | H | H | H |
| 156 | 4-Cl | H | H | COOH | H | H | H | H | CH3 | H |
| 157 | 4-Cl | H | H | H | COOH | H | H | H | H | H |
| 158 | 4-Cl | H | H | H | COOH | H | H | H | CH3 | H |
| 159 | 4-Cl | H | H | COOH | H | H | H | 5-Cl | H | H |
| 160 | 4-Cl | H | H | COOH | H | H | H | 5-Cl | CH3 | H |
| 161 | 4-Cl | H | H | H | COOH | H | H | 6-Cl | H | H |
| 162 | 4-Cl | H | H | H | COOH | H | H | 6-Cl | CH3 | H |
| 163 | 4-Cl | H | H | COOH | H | H | H | 4-Cl | H | H |
| 164 | 4-Cl | H | H | COOH | H | H | H | 4-Cl | CH3 | H |
| 165 | 4-Br | H | H | COOH | H | H | H | H | H | H |
| 166 | 4-Br | H | H | COOH | H | H | H | H | CH3 | H |
| 167 | 4-Br | H | H | H | COOH | H | H | H | H | H |
| 168 | 4-Br | H | H | H | COOH | H | H | H | CH3 | H |
| 169 | 4-Br | H | H | COOH | H | H | H | 5-Cl | H | H |
| 170 | 4-Br | H | H | COOH | H | H | H | 5-Cl | CH3 | H |
| 171 | 4-Br | H | H | H | COOH | H | H | 6-Cl | H | H |
| 172 | 4-Br | H | H | H | COOH | H | H | 6-Cl | CH3 | H |
| 173 | 4-Br | H | H | COOH | H | H | H | 4-Cl | H | H |
| 174 | 4-Br | H | H | COOH | H | H | H | 4-Cl | CH3 | H |
| 175 | 2-MeO | H | H | COOH | H | H | H | H | H | H |
| 176 | 2-MeO | H | H | COOH | H | H | H | H | CH3 | H |
| 177 | 2-MeO | H | H | H | COOH | H | H | H | H | H |
| 178 | 2-MeO | H | H | H | COOH | H | H | H | CH3 | H |
| 179 | 2-MeO | H | H | COOH | H | H | H | 5-Cl | H | H |
| 180 | 2-MeO | H | H | COOH | H | H | H | 5-Cl | CH3 | H |
| 181 | 2-MeO | H | H | H | COOH | H | H | 6-Cl | H | H |
| 182 | 2-MeO | H | H | H | COOH | H | H | 6-Cl | CH3 | H |
| 183 | 2-MeO | H | H | COOH | H | H | H | 4-Cl | H | H |
| 184 | 2-MeO | H | H | COOH | H | H | H | 4-Cl | CH3 | H |
| 185 | 3-MeO | H | H | COOH | H | H | H | H | H | H |
| 186 | 3-MeO | H | H | COOH | H | H | H | H | CH3 | H |
| 187 | 3-MeO | H | H | H | COOH | H | H | H | H | H |
| 188 | 3-MeO | H | H | H | COOH | H | H | H | CH3 | H |
| 189 | 3-MeO | H | H | COOH | H | H | H | 5-Cl | H | H |
| 190 | 3-MeO | H | H | COOH | H | H | H | 5-Cl | CH3 | H |
| 191 | 3-MeO | H | H | H | COOH | H | H | 6-Cl | H | H |
| 192 | 3-MeO | H | H | H | COOH | H | H | 6-Cl | CH3 | H |
| 193 | 3-MeO | H | H | COOH | H | H | H | 4-Cl | H | H |
| 194 | 3-MeO | H | H | COOH | H | H | H | 4-Cl | CH3 | H |
| 195 | 4-MeO | H | H | COOH | H | H | H | H | H | H |
| 196 | 4-MeO | H | H | COOH | H | H | H | H | CH3 | H |
| 197 | 4-MeO | H | H | H | COOH | H | H | H | H | H |
| 198 | 4-MeO | H | H | H | COOH | H | H | H | CH3 | H |
| 199 | 4-MeO | H | H | COOH | H | H | H | 5-Cl | H | H |
| 200 | 4-MeO | H | H | COOH | H | H | H | 5-Cl | CH3 | H |
| 201 | 4-MeO | H | H | H | COOH | H | H | 6-Cl | H | H |
| 202 | 4-MeO | H | H | H | COOH | H | H | 6-Cl | CH3 | H |
| 203 | 4-MeO | H | H | COOH | H | H | H | 4-Cl | H | H |
| 204 | 4-MeO | H | H | COOH | H | H | H | 4-Cl | CH3 | H |
| 205 | 2-NO2 | H | H | COOH | H | H | H | H | H | H |

-continued

| Example | R1 | R2 | R3 | R4 | R5 | R6 | R7 | R8 | R9 | R10 |
|---------|------|------|----|------|------|----|----|------|-----|-----|
| 206 | 2-NO2 | H | H | COOH | H | H | H | H | CH3 | H |
| 207 | 2-NO2 | H | H | H | COOH | H | H | H | H | H |
| 208 | 2-NO2 | H | H | H | COOH | H | H | H | CH3 | H |
| 209 | 2-NO2 | H | H | COOH | H | H | H | 5-Cl | H | H |
| 210 | 2-NO2 | H | H | COOH | H | H | H | 5-Cl | CH3 | H |
| 211 | 2-NO2 | H | H | H | COOH | H | H | 6-Cl | H | H |
| 212 | 2-NO2 | H | H | H | COOH | H | H | 6-Cl | CH3 | H |
| 213 | 2-NO2 | H | H | COOH | H | H | H | 4-Cl | H | H |
| 214 | 2-NO2 | H | H | COOH | H | H | H | 4-Cl | CH3 | H |
| 215 | 3-NO2 | H | H | COOH | H | H | H | H | H | H |
| 216 | 3-NO2 | H | H | COOH | H | H | H | H | CH3 | H |
| 217 | 3-NO2 | H | H | H | COOH | H | H | H | H | H |
| 218 | 3-NO2 | H | H | H | COOH | H | H | H | CH3 | H |
| 219 | 3-NO2 | H | H | COOH | H | H | H | 5-Cl | H | H |
| 220 | 3-NO2 | H | H | COOH | H | H | H | 5-Cl | CH3 | H |
| 221 | 3-NO2 | H | H | H | COOH | H | H | 6-Cl | H | H |
| 222 | 3-NO2 | H | H | H | COOH | H | H | 6-Cl | CH3 | H |
| 223 | 3-NO2 | H | H | COOH | H | H | H | 4-Cl | H | H |
| 224 | 3-NO2 | H | H | COOH | H | H | H | 4-Cl | CH3 | H |
| 225 | 4-NO2 | H | H | COOH | H | H | H | H | H | H |
| 226 | 4-NO2 | H | H | COOH | H | H | H | H | CH3 | H |
| 227 | 4-NO2 | H | H | H | COOH | H | H | H | H | H |
| 228 | 4-NO2 | H | H | H | COOH | H | H | H | CH3 | H |
| 229 | 4-NO2 | H | H | COOH | H | H | H | 5-Cl | H | H |
| 230 | 4-NO2 | H | H | COOH | H | H | H | 5-Cl | CH3 | H |
| 231 | 4-NO2 | H | H | H | COOH | H | H | 6-Cl | H | H |
| 232 | 4-NO2 | H | H | H | COOH | H | H | 6-Cl | CH3 | H |
| 233 | 4-NO2 | H | H | COOH | H | H | H | 4-Cl | H | H |
| 234 | 4-NO2 | H | H | COOH | H | H | H | 4-Cl | CH3 | H |
| 235 | 4-N(CH3)2 | H | H | COOH | H | H | H | H | H | H |
| 236 | 4-N(CH3)2 | H | H | COOH | H | H | H | H | CH3 | H |
| 237 | 4-N(CH3)2 | H | H | H | COOH | H | H | H | H | H |
| 238 | 4-N(CH3)2 | H | H | H | COOH | H | H | H | CH3 | H |
| 239 | 4-N(CH3)2 | H | H | COOH | H | H | H | 5-Cl | H | H |
| 240 | 4-N(CH3)2 | H | H | COOH | H | H | H | 5-Cl | CH3 | H |
| 241 | 4-N(CH3)2 | H | H | H | COOH | H | H | 6-Cl | H | H |
| 242 | 4-N(CH3)2 | H | H | H | COOH | H | H | 6-Cl | CH3 | H |
| 243 | 4-N(CH3)2 | H | H | COOH | H | H | H | 4-Cl | H | H |
| 244 | 4-N(CH3)2 | H | H | COOH | H | H | H | 4-Cl | CH3 | H |
| 245 | 2-Cl | 4-Cl | H | COOH | H | H | H | H | H | H |
| 246 | 2-Cl | 4-Cl | H | COOH | H | H | H | H | CH3 | H |
| 247 | 2-Cl | 4-Cl | H | H | COOH | H | H | H | H | H |
| 248 | 2-Cl | 4-Cl | H | H | COOH | H | H | H | CH3 | H |
| 249 | 2-Cl | 4-Cl | H | COOH | H | H | H | 5-Cl | H | H |
| 250 | 2-Cl | 4-Cl | H | COOH | H | H | H | 5-Cl | CH3 | H |
| 251 | 2-Cl | 4-Cl | H | H | COOH | H | H | 6-Cl | H | H |
| 252 | 2-Cl | 4-Cl | H | H | COOH | H | H | 6-Cl | CH3 | H |
| 253 | 2-Cl | 4-Cl | H | COOH | H | H | H | 4-Cl | H | H |
| 254 | 2-Cl | 4-Cl | H | COOH | H | H | H | 4-Cl | CH3 | H |
| 255 | 3-Cl | 4-Cl | H | COOH | H | H | H | H | H | H |
| 256 | 3-Cl | 4-Cl | H | COOH | H | H | H | H | CH3 | H |
| 257 | 3-Cl | 4-Cl | H | H | COOH | H | H | H | H | H |
| 258 | 3-Cl | 4-Cl | H | H | COOH | H | H | H | CH3 | H |
| 259 | 3-Cl | 4-Cl | H | COOH | H | H | H | 5-Cl | H | H |
| 260 | 3-Cl | 4-Cl | H | COOH | H | H | H | 5-Cl | CH3 | H |
| 261 | 3-Cl | 4-Cl | H | H | COOH | H | H | 6-Cl | H | H |
| 262 | 3-Cl | 4-Cl | H | H | COOH | H | H | 6-Cl | CH3 | H |
| 263 | 3-Cl | 4-Cl | H | COOH | H | H | H | 4-Cl | H | H |
| 264 | 3-Cl | 4-Cl | H | COOH | H | H | H | 4-Cl | CH3 | H |

Smooth Muscle Relaxing Activity

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37 deg.C.) physiological salt solution (PSS) of the following composition (mM): NaCl, 118.4; KCl, 4.7; $CaCl_2$, 2.5; $MgSO_4$, 4.7; $H_2O$, 1.2 $NaHCO_3$, 24.9; $KH_2PO_4$, 1.2; glucose, 11.1; EDTA, 0.023; gassed with 95% $O_2$; ⅖% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 $\mu M$ carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 $\mu$M.

The results of this study are shown in Table I.

TABLE I

Inhibition of Contractions in Isolated Rat Bladder Strips and Indication of Selectivity

| Example # | n | $IC_{50}/\mu M$ Bladder(B) | n | $IC_{50}/\mu M$ Aorta(A) | $IC_{50}(A)/IC_{50}(B)$ |
|---|---|---|---|---|---|
| 1, Step 3 | 4 | 3.7 ± 2.1 | 5 | 61.2 ± 9.2 | 16.5 |
| 1, Step 4 | 6 | 1.07 ± 0.37 | 6 | 41.9 ± 8.4 | 39.6 |
| 2 | 2 | 14.1 ± 1.77 | 4 | 118.2 ± 27.6 | 8.4 |
| 3 | 4 | 4.9 ± 2.6 | 3 | 53.5 ± 7 | 11 |
| 4 | 7 | 3.37 ± 0.59 | 3 | 39.5 ± 12 | 11.7 |
| 5 | 6 | 5.3 ± 2.8 | 7 | 146 ± 49 | 27.5 |
| 6 | 5 | 18.1 ± 4.2 | — | — | — |
| 7 | 4 | 7.4 ± 4 | — | — | — |
| 8 | 4 | 1.18 ± 0.45 | 3 | 4.23 ± 0.66 | 3.58 |
| 9 | 2 | 0.52 ± 0.24 | 3 | 2.76 ± 1.63 | 5.31 |
| 10 | 4 | 1.44 ± 0.85 | 3 | 6.93 ± 12.4 | 4.81 |
| 11 | 6 | 3.45 ± 0.75 | — | — | — |
| 12 | 3 | 11.4 ± 3.8 | — | — | — |
| 13 | 2 | 9.6 ± 7.4 | — | — | — |
| 14 | 3 | 10.8 ± 0.6 | — | — | — |
| 14 | 3 | I = 35.6 ± 5%* | — | — | — |
| Tranilast ®§ | 2 | 14.4 ± 4.5 | 5 | 15.59 ± 8.96 | 1.08 |

§Tranilast is (E)-2-[3-(3,4-Dimethoxy-phenyl)-acryloylamino]-benzoic acid.
*Percent inhibition at 30 $\mu$M In addition, we tested the ability of compounds to inhibit the hyperactivity of hypertrophied bladder (detrussor) smooth muscle in conscious female rats with hypertrophied bladders and thereby alleviate urinary incontinence in rats according to the following protocol described by Malmgrem (A. Malmgrem, K. E. Andersson, C. Sjogren, P. O. Andersson, Effects of Pinacidil and Cromakalim (BRL 34915) on Bladder Function in Rats with Detrusor Instability, J. Urol. 142:1134, 1989.):

Female Sprague-Dawley rats, ranging in weight from 190–210 g are used. Up to 25 animals are prepared each time. After development of bladder hypertrophy 4–8 animals are used per test.

Compounds are dissolved in PEG-200 and administered by gastric gavage or intraveneously in a volume of 5 mL/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4-0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals are allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 min to rest before the saline infusion (20 mL/hr for 20 minutes) is started for the first cystometry period. Two hours after the first cystometry period, the rats are dosed with the vehicle or the test compound and one hour later a second cystometry is performed.

The following urodynamic variables are recorded:

Basal bladder pressure=the lowest bladder pressure during cystometry

Threshold pressure=bladder pressure immediately prior to micturition

Micturition volume=volume expelled

Micturition pressure=peak pressure during voiding

Spontaneous activity=mean amplitude of bladder pressure fluctuations during filling Presentation of results:

The mean value of each variable is calculated before and after compound administration. For each compound the changes in the variables measured are compared to the values obtained before treatment and expressed as percent inhibition. The data are also subjected to 2-way analysis of variance to determine significant ($p<0.05$) changes in the variable measured.

Criteria for Activity:

The most characteristic finding in this rat model is spontaneous bladder contractions which develop during filling. The compounds which inhibit spontaneous contractions by at least 50% at 10 mg/kg p.o. or i.v. (arbitrary chosen dose) are considered active.

The results of this study are shown in Table II

TABLE II

Inhibition of Spontaneous Contractions In Vivo

| Compound | # of animals | dose mg/kg (i.v.) | % Red (F)* |
|---|---|---|---|
| Example 9 | 10 | 30 | −71 ± 6 |

*percent reduction in the total number of spontaneous contractions in the hypertrophied rat bladder model Potassium Channel Activation Potassium channel activation by compounds of the present invention was established by examining the effect of the compound of Example 1 on calcium-dependent large conductance potassium channels (maxi K$^+$) as follows:

Rat detrusor cells were isolated in a manner previously described for guinea-pig detrusor (Sheldon and Argentieri, 1995). Male Sprage-Dawley rats (200–400 grams) were euthanized by $CO_2$ inhalation and exsanguination. Their urinary bladders were rapidly removed and placed in 37° C. physiological solution with the following composition (mM): Na glutamate (80.0), NaCl (54.7), KCl (5.0), NaHCO$_3$ (25.0), MgCl$_2$.2H$_2$O (2.5), D-glucose (11.8) and CaCl$_2$ (0.2) gassed with CO$_2$—O$_2$, 95%/5% for a final pH of 7.4. The dome of the bladder was isolated from the trigon region and the mucosa was removed. This tissue was then cut into 2–3 mm wide strips and placed in fresh buffer for 1 hour. Tissues were then transferred into 10.0 ml of an isolation buffer containing the above composition plus collagenase type VIII (1.0 mg/ml) and pronase (0.25 mg/ml). After 10 minutes the isolation buffer was replaced with fresh isolation buffer for an additional 10 min. The tissue was then washed 3 times in fresh collagenase and pronase free solution and stored at room temperature until studied. Cells for study were prepared by triturating 1–2 pieces of detrusor tissue in 2 mL of fresh isolation buffer for 5 minutes with a polished Pasteur pipette, (tip diameter~1.5 ml) attached to a modified Harvard Respirator pump (Harvard Apparatus, Southnatic, Mass.) at a rate of 20x/min. with an approximate volume of 5 mL. Cells were then placed on a microscope stage in a temperature regulated tissue bath at 32.5° C. and continually superfused with physiological salt solution (PSS) that contained the following (mM): NaCl (118.4), KCl (4.7), CaCl$_2$ (2.5), MgSO$_4$ (1.2), KH$_2$PO$_4$ (1.2), NaHCO$_3$ (24.9) and D-glucose (11.1) gassed with CO$_2$—O$_2$, 95%/5% to achieve a pH of 7.4.

Single cell recordings were performed with a List-Medical EPC-7 patch clamp amplifier (Adams & List Assoc., Westbury, N.Y.). Pipette electrodes had tip resistances of 2–4 MΩ and were filled with the following composition (mM): KCl (126.0), MgCl$_2$.6H$_2$O (4.5), ATP Mg salt (4.0), GTP tris salt (0.3), creatine PO$_4$ (14.0), D-glucose (9.0), EGTA (9.0), HEPES (9.0). The pH was adjusted to 7.4 with KOH. Signals were acquired (3 kHz high frequency cut-off) using a 586-based personal computer and pClamp (Axon Instruments, Foster City, Calif.) software.

Whole cell recordings were made using broken patch assess. Currents were evoked using either voltage steps (Vh=−50; Vt=−60 to 40 mV) or voltage ramps (−60 to 40 mV at 3.3 mV/sec.). After stability was achieved control currents were recorded. Next, WAY-131354-A (10 μM) was added to the superfusate. Currents were recorded for 5 to 10 minutes or until compound effects reached steady state. This was followed either by washout or addition of glyburide (5 μM) to the superfusate.

Results

Figure 1B:
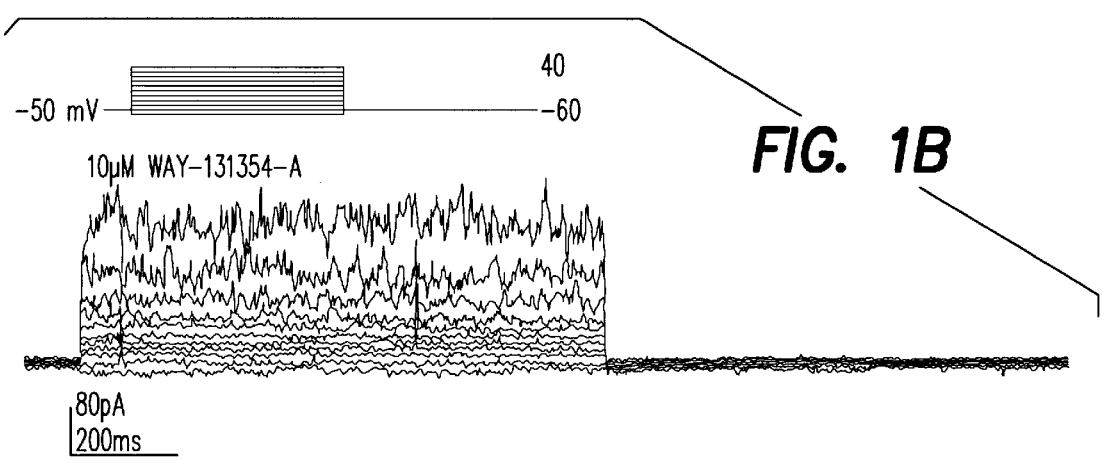
FIG. 1B shows cell outward current following exposure of cells to compound of Example 1.
Figure 1C:
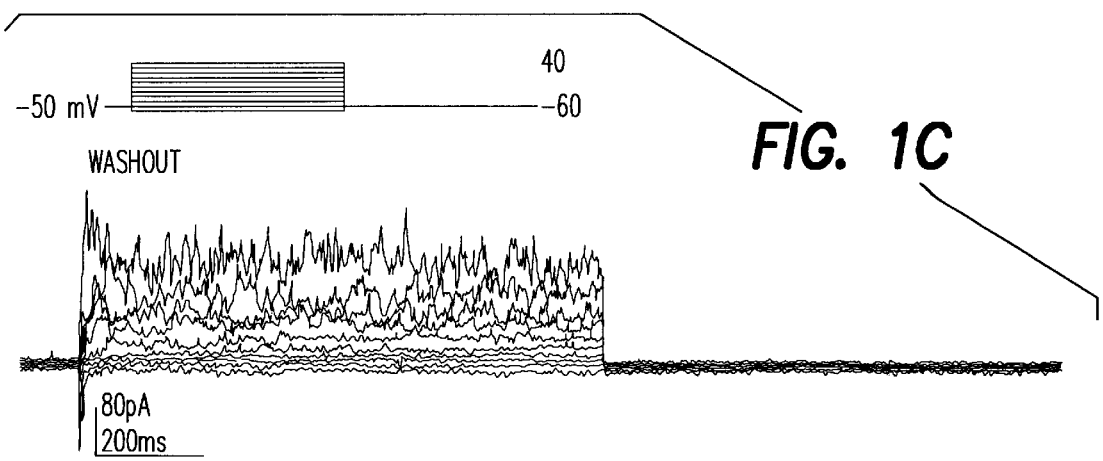
FIG. 1C shows cell outward current following washout.

All cells exposed to Example 1 (dissolved in DMSO and further diluted in PSS) responded with an increase in outward current that was reversible upon washout (FIG. 1). Exposure to the sulfonyl urea glyburide had no effect (data not shown). Previous studies have shown that this current is iberiotoxin sensitive which is a hallmark of the maxi K$^+$ channel. It is concluded therefore, that the compound of Example 1 is capable of activating the maxi K$^+$ current in isolated rat bladder cells consistent with its ability to inhibit KCl-induced contractions of intact tissue in vitro.

Chloride Channel Blockade

The ability of compounds of the present invention to act as chloride channel blockers was established as follows.

Normal human bronchial epithelial cells (NHBE) were commercially available from Clonetics Corporation (San Diego, Calif.) and bladder cells were isolated from rat bladder.

The normal external solution contained (in mM): N-methyl d-Glucamine chloride (NMDGCl). 140, MgCl$_2$ 2, CaCl$_2$ 2 and 4-(2-hydroxyethyl)-1-piperazine ethane-sulfonic acid (HEPES) 10. The normal pipette solution contained (in mM): NMDGCl. 125, HEPES 10, MgCl$_2$ 2, ethylenebis(oxonitrilo)tetraacetate (EGTA) 2, and ATP$_{Mg}$5, the pH adjusted to 7.3 with TRIS. To identify the leak conductance from depolarization, internal Cl ion concentration was reduced to 40 mM using glutamic acid (E$_{Cl}$ approximately −31 mV according Nernst equation). The osmolarity for standard external solution was about 280 mOsm. Hypotonic solutions were obtained by diluting the normal external solution with distilled water.

The whole cell voltage clamp recording techniques were utilized to record membrane ionic currents. The volume of the recording chamber was 1 ml and the rate of superfusion was 4 ml/min. Membrane currents were recorded using an Axopatch 200A Patch Clamp Amplifier (Axon Instruments, Inc., Foster City, Calif.). Under voltage clamp conditions, the cells were stimulated at 0.2 Hz to be sure channels were completely recovered between two voltage steps. Membrane currents were generated by following three protocols: 1) For monitoring; Vh (holding potential)=−30 mV, Vc (clamp potential)=60 mV and Tc (clamp time)=1 s. 2) For ramp test; Vh=−30 mV, V$_{Ramp}$ (ramp potential range)=from −100 to 100 mV, T$_{Ramp}$=3 s. 3). For current-voltage curve (I–V); Vh=−30 mV, Vc=from −100 to 100 mV with 10 mV step and Tc=1 s.

The effects of compounds of Formula I on chloride currents was evaluated in normal human broncheolar epithelial cells (NHBE) and guinea pig bladder and are summarized in the table below:

| Test | Preparation | Type of I$_{Cl}$ | % blockade 10 μM | % blockade 20 μM | Washable |
|---|---|---|---|---|---|
| 1 | NHBE | CFTR | 23% | 80% | Yes |
| 2 | NHBE | CFTR |  | 96% | Yes |
| 3 | Bladder | Swelling |  | 67% | Yes |
| 4 | NHBE | CFTR |  | 71% | n/a |
| 5 | NHBE | CFTR |  | 79% | Yes |
| 6 | NHBE | CFTR |  | 98% | Yes |
|   |   |   |   | 0.82 +− 0.05; n = 6 |   |

CFTR = cystic fibrosis transregulatory chloride channel

Figure 2A:
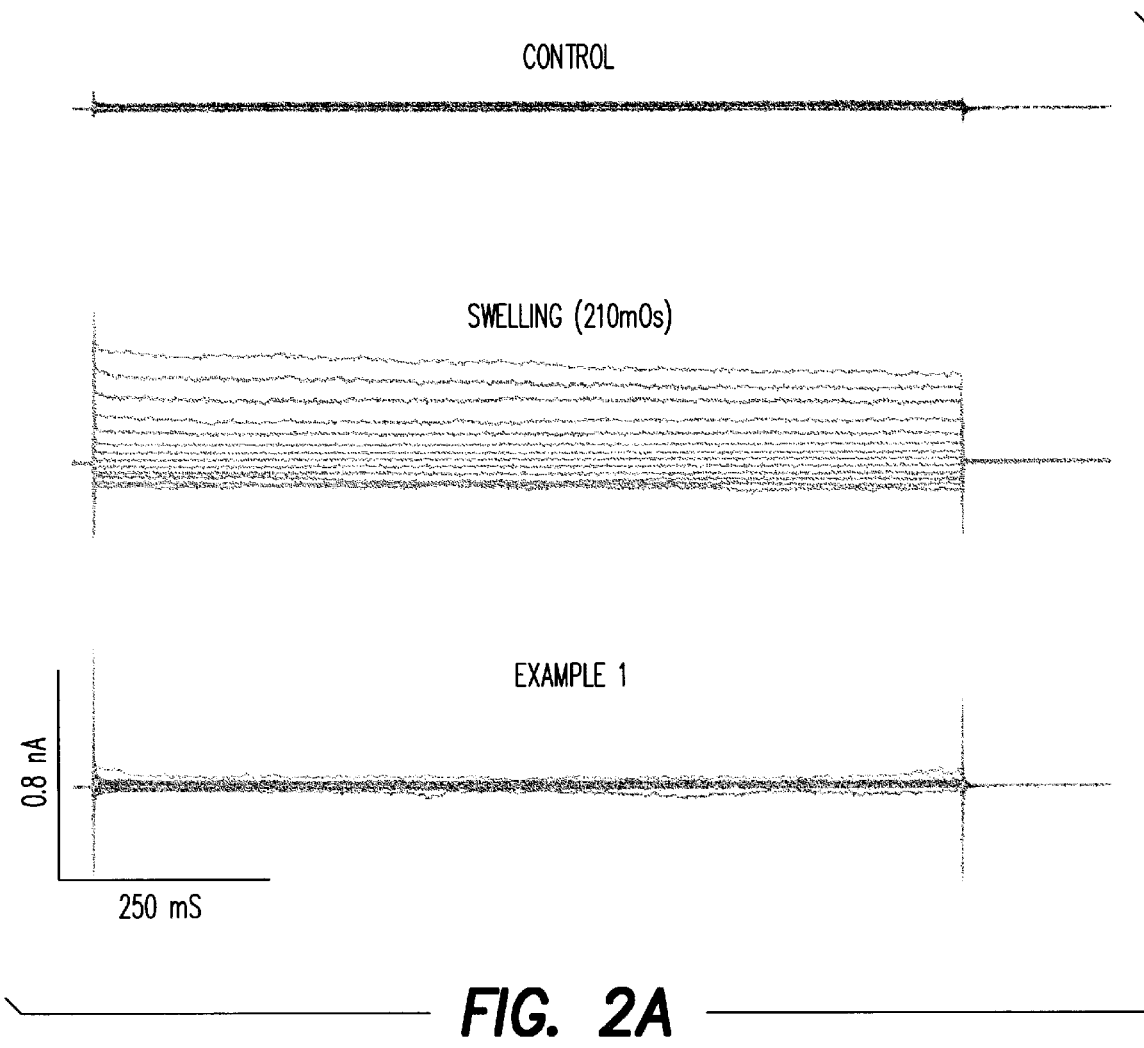
FIG. 2A depicts current traces for a cell in isotonic, low osmolarity and after exposure to Example 1.
Figure 2B:
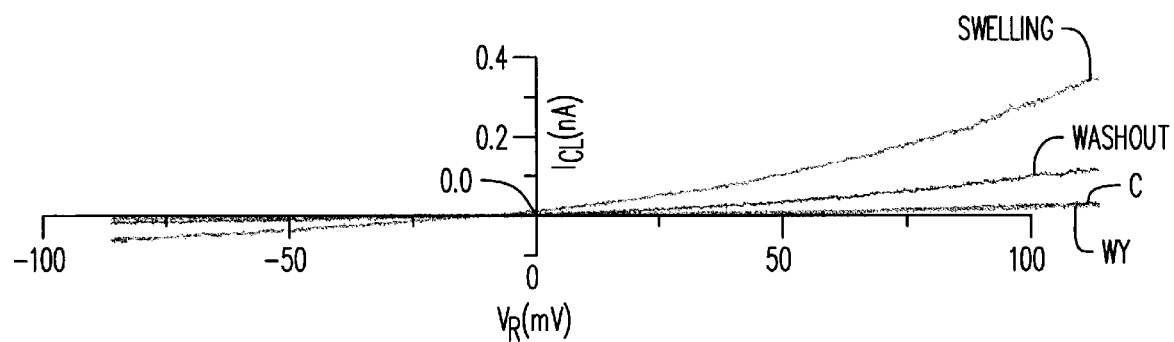
FIG. 2B depicts voltage dependency of current recorded in the presence of control (C), hypotonic (swelling), Example 1(WY) and washout solutions (washout).
Figure 2C:
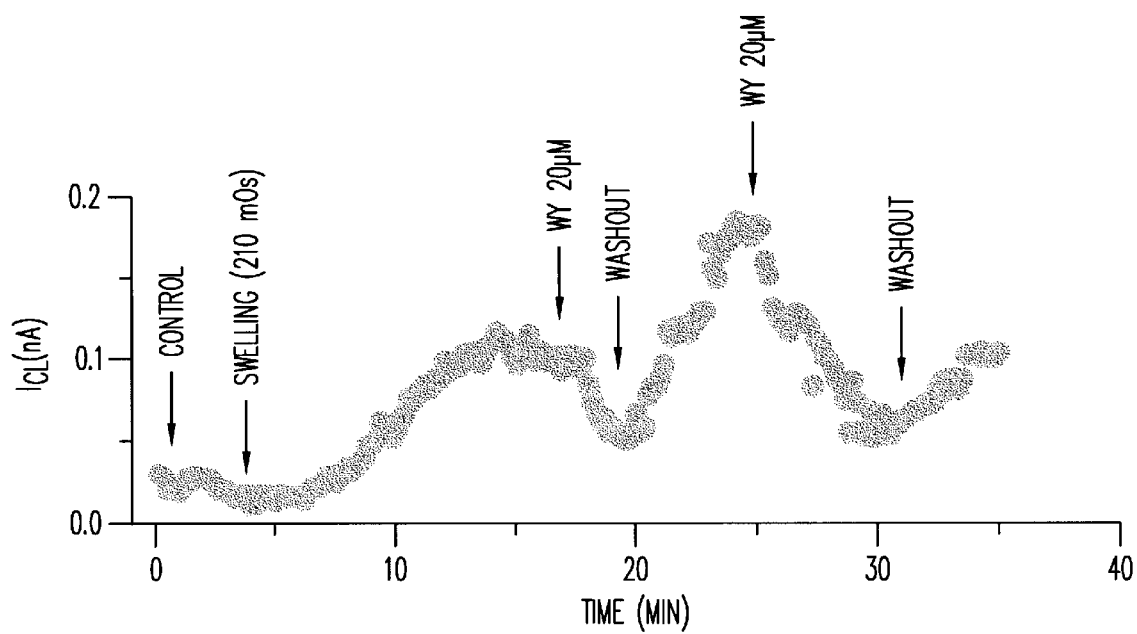
FIG. 2C depicts the time course of the effect on Example 1 on chloride channel current.

FIG. 2 shows that Example 1 inhibited swelling induced chloride channel current on guinea pig bladder cell. A: current traces from −100 to 60 mV were recorded in the isotonic, low osmolarity (210 mOsm) and after application of 20 μM Example 1 in same cell. Example 1 significantly reduced swelling induced chloride current. Panel B is four superimposed ramp test traces recorded in the presence of control, hypotonic, Example 1 and washout solutions. The C panel depicts the time course of the effect of Example 1 on I$_{Cl,swelling}$ at 60 mV monitored from the same cell. The figure shows that I$_{Cl,swelling}$ reached a steady state within 15 min following the addition of 210 mOs solution and with a 67% block in presence of 20 μM Example 1.

Hence, the compounds of this invention have a pronounced effect on smooth muscle contractility and are useful in the treatment of gastrointestinal, cardiovascular, metabolic and central nervous system disorders such as urinary incontinence, irritable bladder and bowel disease, asthma, hypertension, stroke, cystic fibrosis, cardiac arrhythmias, peripheral vascular disease, congestive heart failure, anxiety neurodegenerative disease. and similar diseases as mentioned above, which are amenable to treatment with potassium channel activating and/or chloride channel blocking compounds by administration, orally, parenterally, or by aspiration to a patient in need thereof.

What is claimed is:
1. A compound having the formula:

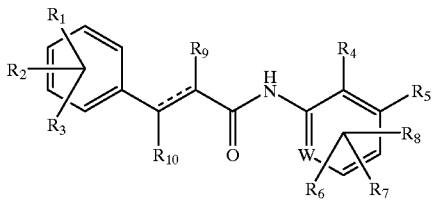

(I)

wherein:
R$_1$, R$_2$ and R$_3$ are, independently, hydrogen, cyano, C$_{1-10}$ perhaloalkoxy, sulfonic acid, C$_{1-10}$ alkylsulfonyl, C$_{6-12}$ arylsulfonyl, C$_{6-12}$ aralkylsulfonyl, C$_{1-10}$ alkylsulfinyl, C$_{6-12}$ arylsufinyl, C$_{6-12}$ aralkylsulfinyl, sulfamoyl, C$_{1-10}$ alkylsulfamido, C$_{6-12}$ arylsulfamido, C$_{1-10}$ alkanoyl, C$_{6-12}$ aryloyl, C$_{6-12}$ aralkanoyl, amino, C$_{1-10}$ alkylamino, C$_{2-10}$ dialkylamino, C$_{6-12}$ aralkylamino, C$_{6-12}$ arylamino, carboxamido, C$_{1-10}$ alkylcarboxamido, C$_{6-12}$ arylcarboxamido, C$_{1-10}$ perhaloalkyl; with the provisos: (1) that R$_1$, R$_2$ and R$_3$ may not all simultaneously be hydrogen, (2) when R$_1$ and R$_2$ are hydrogen, R$_3$ may not be meta-CF$_3$;
R$_4$, R$_5$, R$_6$, R$_7$ and R$_8$ are, independently, hydrogen, COOR$_{15}$, halogen, nitro, cyano, C$_{1-10}$ alkoxy, C$_{1-10}$ haloalkoxy, sulfonic acid, C$_{1-10}$ alkylsulfonyl, C$_{6-12}$ arylsulfonyl, C$_{6-12}$ aralkylsulfonyl, C$_{1-10}$ alkylsulfinyl, C$_{6-12}$ arylsufinyl, C$_{6-12}$ aralkylsulfinyl, sulfamoyl, C$_{1-10}$ alkysulfamido, C$_{6-12}$ arylsufamido, C$_{1-10}$ alkanoyl, C$_{6-12}$ aryloyl, C$_{6-12}$ aralkanoyl, amino, C$_{1-10}$ alkylamino, C$_{2-10}$ dialkylamino, C$_{6-12}$ aralkylamino, C$_{6-12}$ arylamino, carboxamido, C$_{1-10}$ alkylcarboxamido, C$_{6-12}$ arylcarboxamido, C$_{1-10}$ haloalkyl, C$_{1-10}$ alkyl, C$_{2-10}$ alkenyl, C$_{6-12}$ aryl, and C$_{6-12}$ aralkyl, with the proviso that at least one of R$_4$ and R$_5$ is COOR$_{15}$;
R$_9$ is hydrogen, C$_{1-10}$ alkyl and C$_{1-10}$ haloalkyl;
R$_{10}$ is hydrogen, C$_{1-10}$ alkyl, C$_{1-10}$ haloalkyl, or C$_{2-12}$ alkylidene;
R$_{15}$ is hydrogen, metal cation, acetylamido, alkoxyacetoyl or a related moiety which delivers the carboxylate in vivo;
the dotted line is an optional double bond; with the proviso that when R$_{10}$ is an alkylidene moiety, the bond is absent; and
W is nitrogen or carbon bearing a hydrogen, or R$_4$, R$_5$ or R$_6$ as hereinbefore defined; or pharmaceutical salts thereof.

2. A compound of claim 1 wherein R$_{15}$ is selected from the group consisting of hydrogen, a metal cation, a moiety selected from:

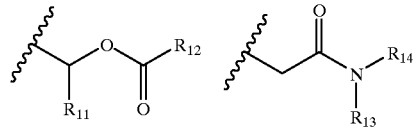

wherein R$_{11}$, R$_{12}$, R$_{13}$, and R$_{14}$ are, independently, hydrogen, C$_{1-10}$ alkyl, C$_{6-12}$ aryl, or C$_{2-12}$ aralkyl.

3. A compound of claim 1 wherein W is carbon bearing a hydrogen.

4. A compound of claim 1 wherein W is nitrogen.

5. A compound of claim 1 wherein at least one of R$_1$, R$_2$ and R$_3$ is C$_{1-6}$ perhaloalkyl.

6. A compound of claim 1 wherein at least one of R$_1$, R$_2$ and R$_3$ is trifluoromethyl.

7. A compound of claim 1 wherein one of R$_1$, R$_2$ and R$_3$ is 4-trifluoromethyl.

8. A comopund of claim 1 wherein at least one of R$_6$, R$_7$ and R$_8$ is a halogen.

9. A compound of claim 1 wherein one of R$_6$, R$_7$ and R$_8$ is 4-chloro.

10. A compound of claim 1 wherein R$_4$ is COOR$_{15}$.

11. A compound of claim 1 wherein R$_4$ is COOH.

12. A compound of claim 1 wherein R$_{10}$ is alkylidene.

13. A compound of claim 1 wherein R$_9$ is C$_{1-6}$ alkyl.

14. A compound of claim 1 wherein R$_9$ is methyl.

15. A compound of claim 1 wherein the double bond is present.

16. A compound of claim 1 which is (E)-2-[2-Methyl-3-(4-trifluoromethyl-phenyl)-acryloylamino]-benzoic acid lithium salt or a pharmaceutical salt thereof.

17. A compound of claim 1 which is 2-[3-(4-Trifluoromethyl-phenyl)propionyl-amino]-benzoic acid or a pharmaceutical salt thereof.

18. A compound of claim 1 which is (E)-2-[3[(4-Trifluoromethyl-phenyl)acryloyl-amino]-benzoic acid or a pharmaceutical salt thereof.

19. A compound of claim 1 which is (E)-2-[3[(4-Trifluoromethyl-phenyl)-acryloylamino]-benzoic acid lithium salt hemihydrate or a pharmaceutical salt thereof.

20. A compound of claim 1 which is 2-[3-(4-Trifluoromethyl-phenyl)-but-3-enoylamino]-benzoic acid or a pharmaceutical salt thereof.

21. A compound of claim 1 which is (E)-2-[3-(4-Trifluoromethyl-phenyl)-but-2-enoylamino]-benzoic acid sodium salt or a pharmaceutical salt thereof.

22. A compound of claim 1 which is (E)-5-Chloro-2-[2-methyl-3-(4-trifluoromethyl-phenyl)-acryloylamino-benzoic acid or a pharmaceutical salt thereof.

23. A compound of claim 1 which is (E)-5-Chloro-2-[2-methyl-3-(4-trifluoromethyl-phenyl)-acryloylamino]-benzoic acid lithium salt hemihydrate or a pharmaceutical salt thereof.

24. A compound of claim 1 which is (E)-4-Chloro-2-[2-methyl-3-(4-trifluoromethyl-phenyl)-acryloylamino]-benzoic acid or a pharmaceutical salt thereof.

25. A compound of claim 1 which is (E)-4-Chloro-2-[2-methyl-3-(4-trifluoromethyl-phenyl)-acryloylamino]-benzoic acid lithium salt hemihydrate or a pharmaceutical salt thereof.

26. A compound of claim 1 which is (E)-2-[2-Methyl-3-(4-trifluoromethyl-phenyl)-acryloylamino]-nicotinic acid or a pharmaceutical salt thereof.

27. A compound of claim 1 which is (E)-5-Methoxy-2-[2-methyl-3-(4-trifluoromethyl-phenyl)-acryloylamino]-benzoic acid or a pharmaceutical salt thereof.

28. A compound of claim 1 which is (E)-2-[2-Methyl-3-(4-trifluoromethyl-phenyl)-acryloylamino]-benzoic acid diethylcarbamoylmethyl ester or a pharmaceutical salt thereof.

29. A pharmaceutical composition comprising a compound having the formula:

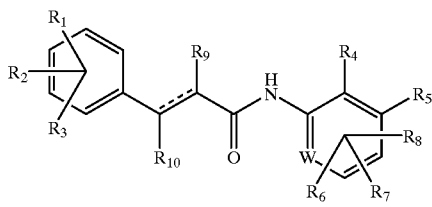

(I)

wherein:

$R_1$, $R_2$ and $R_3$ are, independently, hydrogen, cyano, $C_{1-10}$ perhaloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ perhaloalkyl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$, $R_6$, $R_7$ and $R_8$ are, independently, hydrogen, $COOR_5$, halogen, nitro, cyano, $C_{1-10}$ alkoxy, $C_{1-10}$ haloalkoxy, sulfonic acid, $C_{1-10}$ alkylsulfonyl, $C_{6-12}$ arylsulfonyl, $C_{6-12}$ aralkylsulfonyl, $C_{1-10}$ alkylsulfinyl, $C_{6-12}$ arylsufinyl, $C_{6-12}$ aralkylsulfinyl, sulfamoyl, $C_{1-10}$ alkylsulfamido, $C_{6-12}$ arylsulfamido, $C_{1-10}$ alkanoyl, $C_{6-12}$ aryloyl, $C_{6-12}$ aralkanoyl, amino, $C_{1-10}$ alkylamino, $C_{2-10}$ dialkylamino, $C_{6-12}$ aralkylamino, $C_{6-12}$ arylamino, carboxamido, $C_{1-10}$ alkylcarboxamido, $C_{6-12}$ arylcarboxamido, $C_{1-10}$ haloalkyl, $C_{1-10}$ alkyl, $C_{2-10}$ alkenyl, $C_{6-12}$ aryl, and $C_{6-12}$ aralkyl, with the proviso that at least one of $R_4$ and $R_5$ is $COOR_{15}$;

$R_9$ is hydrogen, $C_{1-10}$ alkyl and $C_{1-10}$ haloalkyl;

$R_{10}$ is hydrogen, $C_{1-10}$ alkyl, $C_{1-10}$ haloalkyl, or $C_{2-12}$ alkylidene;

$R_{15}$ is hydrogen, metal cation, acetylamido, alkoxyacetoyl or a related moiety which delivers the carboxylate in vivo;

the dotted line is an optional double bond; with the proviso that when $R_{10}$ is an alkylidene moiety, the bond is absent; and W is nitrogen or carbon bearing a hydrogen, or $R_4$, $R_5$ or $R_6$ as hereinbefore defined; or pharmaceutical salts thereof.

* * * * *